(12) United States Patent
Flagan et al.

(10) Patent No.: US 9,095,793 B2
(45) Date of Patent: Aug. 4, 2015

(54) RADIAL OPPOSED MIGRATION AEROSOL CLASSIFIER WITH GROUNDED AEROSOL ENTRANCE AND EXIT

(71) Applicant: California Institute of Technology, Pasadena, CA (US)

(72) Inventors: Richard C. Flagan, Pasadena, CA (US); Wilton Mui, Pasadena, CA (US); Andrew J. Downard, Los Angeles, CA (US)

(73) Assignee: California Institute of Technology, Pasadena, CA (US)

( * ) Notice: Subject to any disclaimer, the term of this patent is extended or adjusted under 35 U.S.C. 154(b) by 172 days.

(21) Appl. No.: 13/769,122

(22) Filed: Feb. 15, 2013

(65) Prior Publication Data

US 2013/0213861 A1 Aug. 22, 2013

Related U.S. Application Data

(60) Provisional application No. 61/600,409, filed on Feb. 17, 2012.

(51) Int. Cl.
| | |
|---|---|
| *B07B 7/04* | (2006.01) |
| *B01D 21/00* | (2006.01) |
| *B03C 1/30* | (2006.01) |
| *B03C 3/017* | (2006.01) |
| *B03C 3/14* | (2006.01) |

(Continued)

(52) U.S. Cl.
CPC . *B01D 21/00* (2013.01); *B03C 1/30* (2013.01); *B03C 3/017* (2013.01); *B03C 3/14* (2013.01); *B03C 3/15* (2013.01); *G01N 15/0266* (2013.01)

(58) Field of Classification Search
USPC ......... 209/142, 143; 210/644, 748; 95/28, 58, 95/71, 78
See application file for complete search history.

(56) References Cited

U.S. PATENT DOCUMENTS

| | | | | |
|---|---|---|---|---|
| 4,597,947 | A | * | 7/1986 | Almaula ...................... 422/603 |
| 5,193,688 | A | * | 3/1993 | Giddings ..................... 209/155 |
| 5,242,594 | A | * | 9/1993 | Weinmann et al. ........... 210/634 |

(Continued)

FOREIGN PATENT DOCUMENTS

EP 2352008 8/2011

OTHER PUBLICATIONS

PCT International Search Report and Written Opinion dated May 27, 2013 for PCT Application No. PCT/US2013/026499.

(Continued)

*Primary Examiner* — Terrell Matthews
(74) *Attorney, Agent, or Firm* — Gates & Cooper LLP

(57) ABSTRACT

A radial opposed migration classifier is provided for separating particles in a sample, introducing and removing the particles into and out of the classifier at the same potential. A sample passes through a classification channel having two circular walls. The sample is introduced and exits the classifier through the same plane as the first wall, which is at a different potential from the second wall. A cross-flow fluid enters the classification channel through one of the walls. The cross-flow fluid flows at a first velocity and exits in a first direction through the other wall. An imposed field is applied on the particles in a second direction counter to the first direction of the cross-flow. This causes the particles of a desired size and/or charge to migrate at a second velocity opposite and/or equal to a first velocity of the cross-flow. The particles that travel through the channel are discharged.

28 Claims, 18 Drawing Sheets

(51) Int. Cl.
    B03C 3/15    (2006.01)
    G01N 15/02   (2006.01)

(56)                 References Cited

U.S. PATENT DOCUMENTS 5,606,112   A     2/1997   Flagan et al.
    6,109,119   A  *  8/2000   Jiang et al. ................... 73/865.5
    6,276,534   B1 *  8/2001   Huang et al. ............... 209/139.2
    6,905,029   B2 *  6/2005   Flagan .......................... 209/210
    2004/0050756 A1    3/2004   Flagan
    2004/0159587 A1 *  8/2004   Couture ........................ 209/132
    2005/0006578 A1    1/2005   Rockwood et al.
    2006/0266132 A1   11/2006   Cheng et al.
    2009/0173670 A1    7/2009   Okuda et al.
    2013/0108834 A1 *  5/2013   Sweetland ..................... 428/162

OTHER PUBLICATIONS

Bacher, G., "Charge-reduced nano electrospray ionization combined with differential mobility analysis of peptides, proteins, glycoproteins, noncovalent protein complexes and viruses", Journal of Mass Spectrometry, 36(9), pp. 1038-1052, Sep. 2001.
Baykut, G., et al., "Applying a Dynamic Method to the Measurement of Ion Mobility", Journal of the American Society for Mass Spectrometry, 20(11), pp. 2070-2081, Nov. 2009.
Brunelli, N. A., et al., "Radial Differential Mobility Analyzer for One Nanometer Particle Classification", Aerosol Science and Technology, 43(1), pp. 53-59, Jan. 2009.
Bush, M. F., et al., "Collision Cross Sections of Proteins and Their Complexes: a Calibration Framework and Database for Gas-Phase Structural Biology", Analytical Chemistry, vol. 82, No. 22, pp. 9557-9565, Nov. 15, 2010.
Chen, D. R., et al., "Design and Evaluation of a Nanometer Aerosol Differential Mobility Analyzer (Nano-DMA)", J Aerosol Sci, 1998, vol. 29 No. 5/6, pp. 497-509.
Counterman, A. E., et al., "High-Order Structure and Dissociation of Gaseous Peptide Aggregates that are Hidden in Mass Spectra", Journal of the American Society for Mass Spectrometry, 9(8), pp. 743-759, Aug. 1998.
De Juan, J., et al., "High Resolution Size Analysis of Nanoparticles and Ions: Running a Vienna DMA of Near Optimal Length at Reynolds Numbers Up to 5000", J Aerosol Sci, 1998, vol. 29, No. 5/6, pp. 617-626.
De La Mora, J. F., et al., "The potential of differential mobility analysis coupled to MS for the study of very large singly and multiply charged proteins and protein complexes in the gas phase", Biotechnology Journal, 1(9), pp. 988-997, Sep. 2006.
Downard, A. J., et al., "An Asymptotic Analysis of Differential Electrical Mobility Classifiers", Aerosol Science and Technology, 45(6), pp. 727-739, Apr. 2011.
Fernandez-Maestre, R., et al., "Chemical standards in ion mobility spectrometry", The Analyst, 135(6), pp. 1433-1442, Jun. 2010.
Flagan, R.C., "Opposed Migration Aerosol Classifier (OMAC)", Aerosol Science and Technology, 38(9), pp. 890-899, Jan. 2004.
Gamero-Castano, M., et al., "Mechanisms of electrospray ionization of singly and multiply charged salt clusters", Analytica Chimica Acta, 406, pp. 67-91, Feb. 2000.
Giles, K., et al., "Applications of a travelling wave-based radio-frequency-only stacked ring ion guide", Rapid Communications in Mass Spectrometry, 18(20), pp. 2401-2414, Jan. 2004.
Guevremont, R., et al., "Combined Ion Mobility/Time-of-Flight Mass Spectrometry Study of Electrospray-Generated Ions", Analytical Chemistry, vol. 69, No. 19, pp. 3959-3965, Oct. 1, 1997.
Hodyss, R., et al., "Bioconjugates for Tunable Peptide Fragmentation: Free Radical Initiated Peptide Sequencing (FRIPS)", Journal of the American Chemical Society, 127(36), pp. 12436-12437, Sep. 2005.
Hogan, Jr., C. J., et al., "Ion-Pair Evaporation from Ionic Liquid Clusters", Journal of the American Society for Mass Spectrometry, 21, pp. 1382-1386, Aug. 2010.
Hogan, Jr., C. J., et al., "Ion Mobility Measurements of Nondenatured 12-150 kDa Proteins and Protein Multimers by Tandem Differential Mobility Analysis-Mass Spectrometry (DMA-MS)", Journal of the American Society for Mass Spectrometry, 22(1), pp. 158-172, Jan. 2011.
Hogan, Jr., C. J., et al., "Tandem Differential Mobility Analysis-Mass Spectrometry Reveals Partial Gas-Phase Collapse of the GroEL Complex", Journal of Physical Chemistry B, 115, pp. 3614-3621, Apr. 2011.
Kaddis, C. S., "Sizing Large Proteins and Protein Complexes by Electrospray Ionization Mass Spectrometry and Ion Mobility", Journal of the American Society for Mass Spectrometry, 18(7), pp. 1206-1216, Jul. 2007.
Kaufman, S. L. "Macromolecule Analysis Based on Electrophoretic Mobility in Air: Globular Proteins", Analytical Chemistry, vol. 68, No. 11, pp. 1895-1904, Jun. 1, 1996.
Kaufman, S. L. "Analysis of Biomolecules Using Electrospray and Nanoparticle Methods: the Gas-Phase Electrophoretic Mobility Molecular Analyzer (GEMMA)", Journal of Aerosol Science, vol. 29, No. 5/6, pp. 537-552, 1998.
Kaur-Atwal, G., et al., "Chemical standards for ion mobility spectrometry: a review", International Journal for Ion Mobility Spectrometry, 12(1), pp. 1-14, May 2009.
Knutson, E. O., et al., "Aerosol Classification by Electrical Mobility: Apparatus, Theory, and Applications", Journal of Aerosol Science, vol. 6, pp. 443-451, 1975.
Kulmala, M., et al., "Toward Direct Measurement of Atmospheric Nucleation", Science, vol. 318, Oct. 5, 2007.
Labowsky, M., et al., "Novel ion mobility analyzers and filters", Journal of Aerosol Science, 37(3), pp. 340-362, Mar. 2006.
Lee, M., et al., "Gas-phase peptide sequencing by TEMPO-mediated radical generation", Analyst, 134(8), pp. 1706-1712, Aug. 2009.
Martinez-Lozano, P., et al., "Experimental tests of a nano-DMA with no voltage change between aerosol inlet and outlet slits", J Aerosol Sci, 2006, 37(11), pp. 1629-1642.
Purves, R. W., "Investigation of Bovine Ubiquitin Conformers Separated by High-Field Asymmetric Waveform Ion Mobility Spectrometry: Cross Section Measurements Using Energy-Loss Experiments With a Triple Quadrupole Mass Spectrometer", Journal of the American Society for Mass Spectrometry, 11(8), pp. 738-745, Aug. 2000.
Ramiro, E., et al., "Experimental Validation of a High Resolution Nano-DMA", Journal of Aerosol Science, 35, S749-S758, European Aerosol Conference 2004.
Revercomb, H. E., "Theory of Plasma Chromatography/Gaseous Electrophoresis—a Review", Analytical Chemistry, vol. 47, No. 7, pp. 970-983, Jun. 1975.
Rosser, S., et al., "Vienna-Type DMA of High Resolution and High Flow Rate", Aerosol Science and Technology, 39 (12), pp. 1191-1200, Dec. 2005.
Shvartsburg, A. A., et al., "Separation of Peptide Isomers with Variant Modified Sites by High-Resolution Differential Ion Mobility Spectrometry", Analytical Chemistry, vol. 82, No. 19, pp. 8327-8334, Oct. 1, 2010.
Sohn, C.H., "New Reagents and Methods for Mass Spectrometry-Based Proteomics Investigations", Dissertation (Ph. D.), California Institute of Technology, Pasadena, CA, 2011.
Sun, Q., et al., "Side Chain Chemistry Mediates Backbone Fragmentation in Hydrogen Deficient Peptide Radicals", Journal of Proteome Research, 8, pp. 958-966, 2009.
Tammet, H., "Symmetric Inclined Grid Mobility Analyzer for the Measurement of Charged Clusters and Fine Nanoparticles in Atmospheric Air", Aerosol Science and Technology, 45(4), pp. 468-479, Mar. 2011.
Ude, S., et al., "Molecular monodisperse mobility and mass standards from electrosprays of tetra-alkyl ammonium halides", Journal of Aerosol Science, 36(10), pp. 1224-1237, Oct. 2005.
Viidanoja, J., et al., "Tetraalkylammonium halides as chemical standards for positive electrospray ionization with ion mobility spectrometry/mass spectrometry", Rapid Communications in Mass Spectrometry, 19(21), pp. 3051-3055, Jan. 2005.
Winklmayr, W., et al., "A New Electromobility Spectrometer for the Measurement of Aerosol Size Distributions in the Size Range from 1 to 1000 nm", J Aerosol Sci, 1991, vol. 22, No. 3, pp. 289-296.

(56) References Cited

OTHER PUBLICATIONS

Wittmer, D., "Electrospray Ionization Ion Mobility Spectrometry", Analytical Chemistry, vol. 66, No. 14, pp. 2348-2355, 1994.

Wu, C., et al., "Atmospheric Pressure Ion Mobility Spectrometry of Protonated and Sodiated Peptides", Rapid Communications in Mass Spectrometry, 13(12), pp. 1138-1142, Jan. 1999.

Wu, C., et al., "Electrospray Ionization High-Resolution Ion Mobility Spectrometry-Mass Spectrometry", Analytical Chemistry, vol. 70, No. 23, pp. 4929-4938, Dec. 1, 1998.

Wyttenbach, T., et al., "Gas-Phase Conformation of Biological Molecules: Bradykinin", Journal of the American Chemical Society, 118(35), pp. 8355-8364, 1996.

Zhang, S.-H., et al., "Radial Differential Mobility Analyzer", Aerosol Science and Technology, 1995, 23(3), pp. 357-372.

Zhang, S.-H., et al., "Resolution of the Radial Differential Mobility Analyzer for Ultrafine Particles", J Aerosol Sci, 1996, vol. 27, No. 8, pp. 1179-1200.

* cited by examiner

FIG. 2

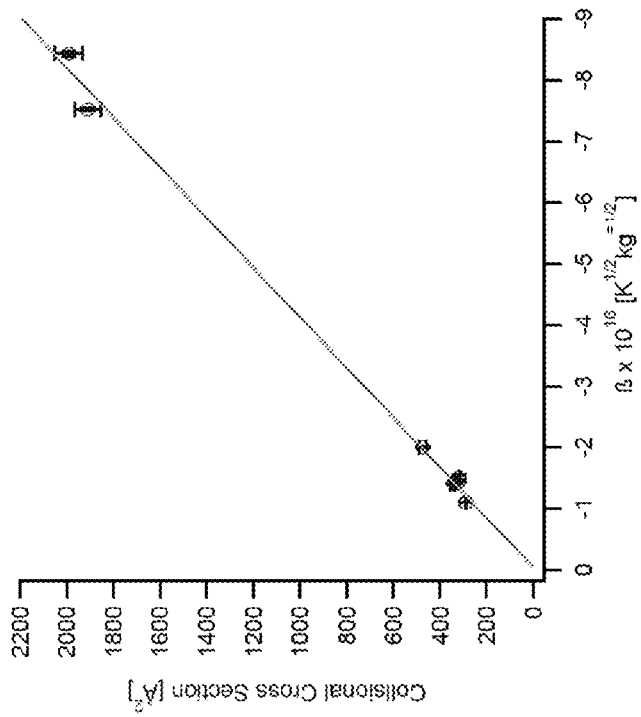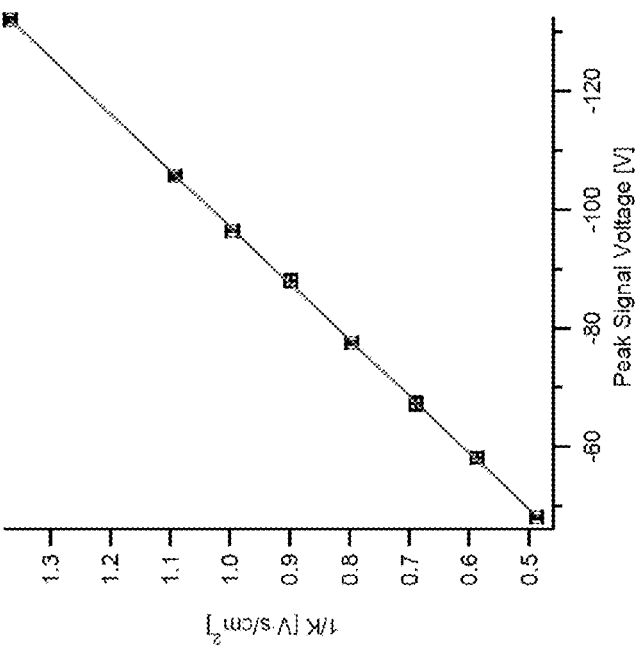
FIG. 11

Tetra-alkyl ammonium halide (TAAX) anion-coordinated singly-charged multimer $\Omega_c$ and $K_{0,c}$.[a]

| TAAX | k Number of TAAX Units | $\Omega_c$ [Å²] | $K_{0,c}$ [cm²V⁻¹s⁻¹] |
|---|---|---|---|
| C2 | 2 | 225±2.7 | 0.94±0.011 |
| C2 | 3 | 256±7.3 | 0.81±0.023 |
| C2 | 4 | 251±3.2 | 0.82±0.010 |
| C2 | 5 | 298±2.7 | 0.69±0.006 |
| C2 | 6 | 325±3.3 | 0.63±0.007 |
| C2 | 7 | 353±4.0 | 0.58±0.007 |
| C2 | 8 | 377±3.4 | 0.54±0.005 |
| C2 | 9 | 405±4.3 | 0.50±0.005 |
| C3 | 2 | 222±3.1 | 0.94±0.013 |
| C3 | 3 | 289±5.8 | 0.71±0.014 |
| C3 | 4 | 333±8.0 | 0.62±0.015 |
| C3 | 5 | 368±4.0 | 0.56±0.006 |
| C3 | 6 | 430±4.1 | 0.48±0.005 |
| C4 | 2 | 250±2.7 | 0.83±0.009 |
| C4 | 3 | 321±3.6 | 0.64±0.007 |
| C4 | 4 | 353±4.8 | 0.58±0.008 |
| C4 | 5 | 399±6.6 | 0.51±0.008 |
| C4 | 6 | 461±5.3 | 0.44±0.005 |
| C5 | 2 | 282±2.5 | 0.73±0.007 |
| C5 | 3 | 354±3.2 | 0.58±0.005 |
| C5 | 4 | 409±4.7 | 0.50±0.006 |
| C5 | 5 | 440±6.1 | 0.46±0.006 |
| C6 | 2 | 310±3.0 | 0.67±0.006 |
| C6 | 3 | 386±3.5 | 0.53±0.005 |
| C6 | 4 | 449±3.8 | 0.46±0.004 |
| C7 | 2 | 335±2.8 | 0.61±0.005 |
| C7 | 3 | 419±3.0 | 0.49±0.004 |
| C7 | 4 | 491±3.7 | 0.42±0.003 |
| C8 | 2 | 361±2.9 | 0.57±0.005 |
| C8 | 3 | 454±2.4 | 0.45±0.003 |
| C12 | 2 | 445±3.7 | 0.46±0.004 |

[a] In $N_2$ at atmospheric pressure and $T_{ESI} = T_2 = 298$ K. Values are the average of three scans. Note that C3 species are iodinated while all other TAAX species are brominated.

FIG. 12

Dominant conformation bradykinin (BK), angiotensin I (AT1), angiotensin II (AT2), and bovine ubiquitin (UB) $\Omega_i$ values.[a]

| Peptide | Peak No. | [b]$\Omega_i$ [Å$^2$] | [c]$\Omega_i$ [Å$^2$] | [d]%Δ | [e]%Δ | [f]%Δ |
|---|---|---|---|---|---|---|
| [\*]BK$^{+1}$ | 3 | 316±3.8 | 261±29.5 | -10.6% | | |
| [#&]BK$^{+1}$ | 5 | 315±2.9 | 260±27.9 | -10.9% | | |
| [\*&]BK$^{+2}$ | 9 | 398±4.8 | 334±30.8 | 4.8% | | -2.8% |
| [#&]BK$^{+2}$ | 11 | 409±5.78 | 343±28.6 | 7.6% | | -0.2% |
| [\*]AT1$^{+1}$ | 13 | 352±3.8 | 292±30.0 | | | |
| [#]AT1$^{+1}$ | 15 | 355±3.0 | 294±28.8 | | | |
| [\*]AT1$^{+2}$ | 18 | 434±8.9 | 365±34.8 | | -5.0% | |
| [#]AT1$^{+2}$ | 20 | 439±4.3 | 369±30.5 | | -4.0% | |
| [\*&]AT1$^{+3}$ | 24 | 568±9.9 | 482±37.0 | | 1.9% | 1.7% |
| [#]AT1$^{+3}$ | 25 | 602±8.5 | 510±31.7 | | 7.9% | 7.7% |
| [\*]AT2$^{+1}$ | 26 | 312±2.7 | 258±28.5 | -9.8% | | |
| [#&]AT2$^{+1}$ | 29 | 315±2.8 | 260±28.0 | -8.9% | | |
| [\*&]AT2$^{+2}$ | 32 | 405±5.0 | 340±31.1 | 7.0% | -4.1% | 1.6% |
| [#&]AT2$^{+2}$ | 34 | 430±14.9 | 362±21.4 | 13.7% | 1.9% | 7.9% |
| [\*]UB$^{+5}$ | 36 | 1636±16.3 | 1390±57.3 | | | |
| [\*]UB$^{+6}$ | 37 | 1895±22.0 | 1613±65.3 | | | |
| [\*&]UB$^{+7}$ | 38 | 2149±25.3 | 1831±71.2 | | | -4.1% |
| [\*&]UB$^{+8}$ | 39 | 2409±231.6 | 2055±79.8 | | | 3.2% |

[a]In $N_2$ at atmospheric pressure and $T_x$ = 298 K. Values are the average of three scans.

[\*]$T_{ESI}$ = 298 K.
[#]$T_{ESI}$ = 400 K.
[&]Peak was used for mobility calibration.
[b]Cross section estimated from instrument calibration (using TAAX ions)
[c]Cross section estimated from mobility calibration (using peptides and proteins)
[d,e,f]Percent difference between this study's mobility calibration $\Omega_i$ value and that published in (d) C. Wu, J. Klasmeier, and H.H. Hill. Atmospheric pressure ion mobility spectrometry of protonated and sodiated peptides. *Rapid Communications in Mass Spectrometry*, 13(12):1138–42, January 1999
(e) G. Baykut, O. von Halem, and O. Raether. Applying a dynamic method to the measurement of ion mobility. *Journal of the American Society for Mass Spectrometry*, 20(11):2070–81, November 2009
(f) M.F. Bush, Z. Hall, K. Giles, J. Hoyes, C.V. Robinson, and B.T. Ruotolo. Collision cross sections of proteins and their complexes: a calibration framework and database for gas-phase structural biology. *Analytical Chemistry*, 82(22):9557–65, November 2010

FIG. 15

RADIAL OPPOSED MIGRATION AEROSOL CLASSIFIER WITH GROUNDED AEROSOL ENTRANCE AND EXIT

CROSS-REFERENCE TO RELATED APPLICATIONS

This application claims the benefit under 35 U.S.C. Section 119(e) of the following co-pending and commonly-assigned U.S. provisional patent application, which is incorporated by reference herein:

Provisional Application Ser. No. 61/600,409, filed on Feb. 17, 2012, by Richard C. Flagan et al., entitled "RADIAL OPPOSED MIGRATION AEROSOL CLASSIFIER WITH GROUNDED AEROSOL ENTRANCE AND EXIT."

This application is also related to the following commonly-assigned patent and patent applications, which are incorporated by reference herein:

U.S. Pat. No. 6,905,029, issued on Jun. 14, 2005, by Richard C. Flagan, entitled "CROSS-FLOW DIFFERENTIAL MIGRATION CLASSIFIER;" and U.S. patent application Ser. No. 13/768,817, filed on Feb. 15, 2013, by Richard C. Flagan et al., entitled "OPPOSED MIGRATION AEROSOL CLASSIFIER GAS AND HEAT EXCHANGER," which claims priority to Provisional Application Ser. No. 61/600,434, filed on Feb. 17, 2012, by Richard C. Flagan et al., entitled "OPPOSED MIGRATION AEROSOL CLASSIFIER GAS AND HEAT EXCHANGER."

BACKGROUND OF THE INVENTION

1. Field of the Invention

The present invention relates generally to separating and measuring particles and molecules in fluids, and in particular, to using a radial cross-flow differential migration classifier to separate and/or measure particles.

2. Description of the Related Art (Note: This application references a number of different publications as indicated throughout the specification by reference numbers enclosed in brackets, e.g., [x]. A list of these different publications ordered according to these reference numbers can be found below in the section entitled "References." Each of these publications is incorporated by reference herein.)

For four decades, the long column differential mobility analyzer (DMA) has been the instrument of choice for the classification of aerosol particles in the 10 nm to 1 micron range [1]. However, there are currently no particle classifiers that are optimal in the sub-10 nm range. One reason is the residence time required for a classifier to effectively separate the particles.

The reduction of column length and the increase of flow rates have led to decreased residence times of samples in a classifier. This has enabled custom instruments to classify particles and gas ions in the range of 1 to 10 nm, where diffusive losses had hampered the performance of standard long column instruments [2-4]. Reductions in residence time have also been obtained by using a radial geometry, which has an inwardly accelerating flow [5-9].

However, in addition to residence time, another important consideration for mobility classifying instruments is its transport efficiency, which is the actual number of particles transmitted divided by the number of particles transmitted if there were no diffusive losses. A major cause for losses is the unfavorable field arising from the voltage transition that nearly all DMAs share [6]. The charged particles have an increased residence time in the neighborhood of the voltage transition. Parasitic fields resulting from static buildups on the dielectric can also further increase losses. Clever instruments have been developed that have eliminated the voltage transition altogether [10,11], but they have not been widely adopted; perhaps partially because of the complexity of determining their transfer function [10].

Altogether, current mobility classification instruments are generally bulky, require expensive blowers or pumps to achieve large flow rates, and require an unfavorable voltage transition at the inlet or outlet that hampers performance and transfer efficiency.

In view of the above, what is needed is a method, apparatus, and article of manufacture for continuously separating particles with enhanced transport efficiency and reduced loss of particles. In particular, there is a need for a method, apparatus, and article of manufacture for separating particles that reduces the diffusive loss of particles due to factors such as voltage transitions and static buildups.

SUMMARY OF THE INVENTION

The invention provided herein has a number of embodiments useful, for example, in separating and measuring particles and molecules in fluids. According to one or more embodiments of the present invention, a radial opposed migration aerosol classifier (ROMAC) is provided for separating and/or measuring particles and molecules in fluids.

In one aspect of the present invention, a radial opposed migration classifier is provided. The radial opposed migration classifier comprises a classification channel through which passes a sample, comprising one or more particles suspended within a sample fluid. The classification channel comprises a first circular wall and a second circular wall that are both permeable to a flow of fluid. The radial opposed migration classifier also comprises a flow distributor channel for introducing the sample into the classification channel. In one or more embodiments, the flow distributor channel comprises a narrowing gap leading into the classification channel. In one or more further embodiments, the sample is introduced tangentially into the flow distributor channel.

A cross-flow fluid enters the classification channel through one of the permeable circular walls. The cross-flow fluid flows at a first velocity and exits in a first direction through the other permeable circular wall. Additionally, an imposed field, including but not limited to an electric, magnetic, thermal, or gravitational field, is applied on the one or more particles in a second direction counter to the first direction of the cross-flow. The imposed field causes the one or more of the particles of a desired size and/or charge to migrate at a second velocity opposite and/or equal to a first velocity of the cross-flow. The particles that travel through the channel are discharged from the radial opposed migration classifier.

In one or more embodiments, the flow distributor channel introduces the sample into the classification channel in the same plane as the first circular wall. Furthermore, the particles that travel through the channel are discharged through a central outlet on the first circular wall.

In further embodiments, the imposed field is an electric field. Particles are introduced into the classification channel through an entrance at an electric potential and discharged from the radial opposed migration classifier through an exit at the same electric potential. In one exemplary application, the particles are discharged at an electrical ground voltage.

In other embodiments, the discharged particles that travel through the channel are classified based on a property of the discharged particles, including but not limited to a size, mass or charge of the discharged particles. In additional embodiments, distributions of the particles with respect to a property of the particles are determined by stepping a strength of the imposed field through a range of values and measuring a concentration of the discharged particles. In other embodiments, distributions of the particles with respect to a property of the particles are determined by stepping a rate of the cross flow through a range of values and measuring a concentration of the discharged particles.

BRIEF DESCRIPTION OF THE DRAWINGS

Referring now to the drawings in which like reference numbers represent corresponding parts throughout:

FIG. 1A is a perspective view of a 2-plane sectional cut of a radial opposed migration aerosol classifier (ROMAC). FIG. 1B is a cross-sectional side view of an assembled ROMAC. FIG. 1C is a photograph of an assembled ROMAC;

FIG. 2 illustrates a revolved volume of the classification region of a radial opposed migration aerosol classifier (ROMAC) in accordance with one or more embodiments of the invention;

FIGS. 11(a)-(b) illustrate a 2-part calibration of a radial opposed migration ion/aerosol classifier (ROMIAC). FIG. 11(a) is a graph depicting the instrument calibration with tetraalkylammonium halides (TAAX), which was not affected by carrier gas contaminants and/or analyte surface concavities. FIG. 11(b) is a graph depicting the mobility calibration with peptides, which was affected by carrier gas contaminants and/or analyte surface concavities;

FIG. 12 is a table detailing the mobility of various TAAX multimers successfully classified with the ROMIAC;

FIG. 15 is a table illustrating the collisional cross-section, $\Omega_i$, as well as the comparison to literature values of the various peptides, bradykinin (BK), angiotensin I (AT1), angiotension II (AT2), and bovine ubiquitin (UB);

FIGS. 16(a)-(h) illustrate the separation by ion mobility-mass spectrometry of model peptide isomers AARAAATAA vs. AATAAARAA and of AARAAHAMA vs. AARAAMAHA, as separated by the ROMIAC. FIGS. 16(c-d, g-h) shows the separation with TEMPO tagged on the peptides.

DETAILED DESCRIPTION OF THE PREFERRED EMBODIMENTS

Figure 1A:
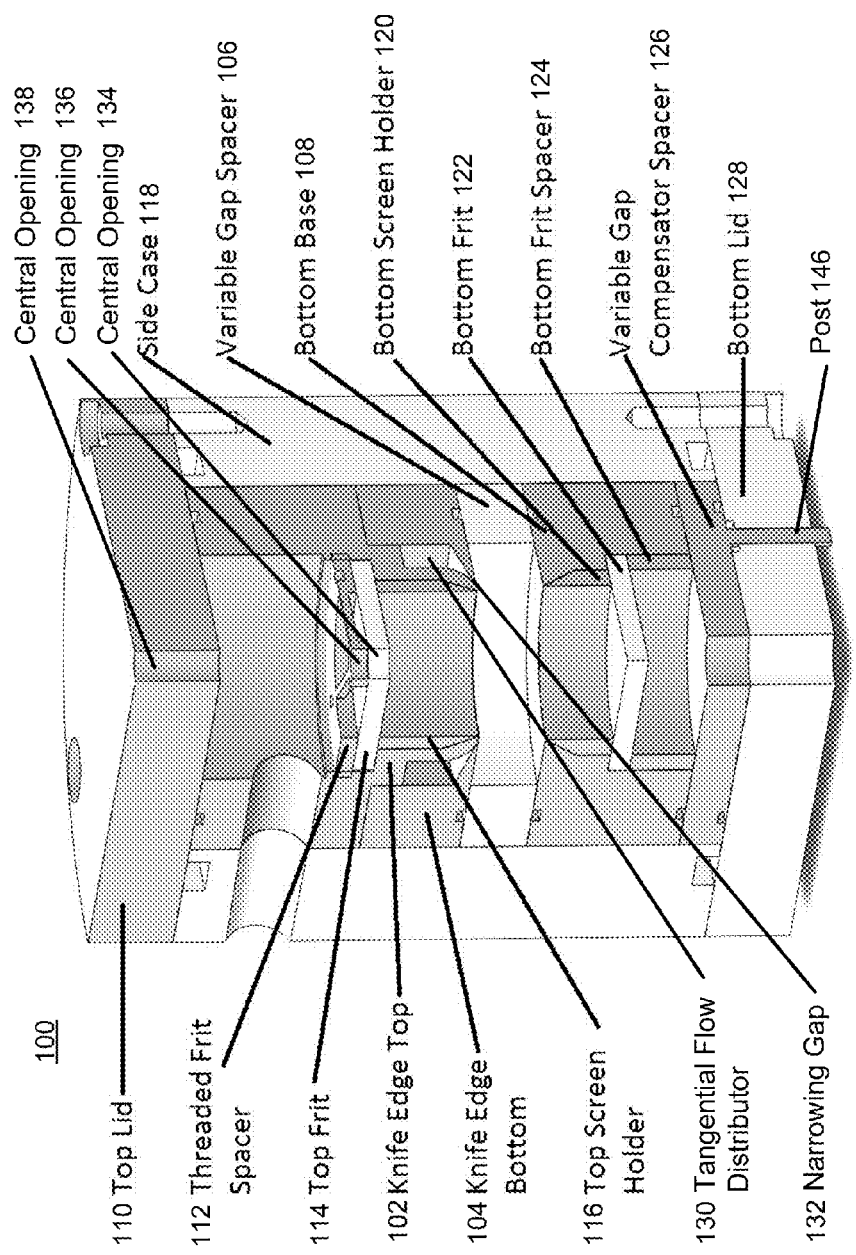
FIGS. 1A-C illustrates various perspective views of an assembled radial migration aerosol classifier (ROMAC) in accordance with one or more embodiments of the invention.

In the following description, reference is made to the accompanying drawings which form a part hereof, and which is shown, by way of illustration, several embodiments of the present invention. It is understood that other embodiments may be utilized and structural changes may be made without departing from the scope of the present invention.

Overview

Opposed migration aerosol classifiers (OMAC) [5] and related inclined grid mobility analyzers (IGMA) [11] scale favorably in their performance relative to DMAs. OMACs in particular can be made much more compact than DMAs and can also classify a broader range of particle diameters than a DMA for fixed flows [12]. For example, a planar-geometry OMAC has been found to be able to differentiate between a bi-disperse mixture of 1.47 nm tetraheptylammonium monomer ions and 1.78 nm tetraheptylammonium dimer ions, with a resolving power of 4.

The OMAC was conceived of as a planar device, and implementations of the related IGMA have all been planar. However, for planar OMACs, some difficulty has been found in obtaining satisfactory internal seals around the rectangular-shaped porous media (i.e., frits, screens) that distribute the cross-flow and serve as the electrodes. Additionally, considerable particle losses have been found in the inlet and outlet regions, on either end of the classification region, owing to the presence of an imposed field without a counteracting cross-flow at these regions. These complications have prevented the instrument from realizing its full potential.

The innovative design features of the radial opposed migration classifier provided herein overcome these complications. In particular, the radial opposed migration classifier addresses the unanticipated difficulties with the fluid flow and electrical field associated with a planar geometry, particularly the unfavorable voltage transitions at the inlet and outlet regions. In one aspect, the radial geometry provides a reduction in the residence time of the particles within the system. In other aspects, the inlet and outlet edge effects and diffusive losses are considerably smaller for a radial geometry when compared to a planar geometry.

In one or more embodiments, both the sample inlet from the flow distributor channel ("race track") and the outlet/classified sample exit are located on the same side of the upper plane of the classification region. In one or more embodiments, the radial opposed migration classifier is a radial opposed migration aerosol classifier (ROMAC) for separating and/or measuring particles in an aerosol. In an exemplary application, the ROMAC allows for aerosol introduction and collection at the same wall/plane. Conventional mobility analysis (e.g. DMA) relies on differential displacement of particles in an electrical field, and thus most initial DMA instrument designers were inclined to locate the aerosol inlet and classified outlet at locations with different potentials. Systems and methods are provided herein where the aerosol is introduced and collected at the same potential, which in one exemplary application is at electric ground voltage for safety reasons. This enhances transport efficiency over alternatives that achieve aerosol classification using a sample inlet and outlet at different voltages.

It should be noted that even though a radial opposed migration aerosol classifier (ROMAC) is used to describe various embodiments of the invention as follows, the radial opposed migration classifier provided herein may be used to separate and measure particles contained in any fluid, including liquids (e.g. colloids or suspensions) and other gases (e.g. atmospheric ultrafine particles), and using any kind of field (e.g. electric, magnetic, thermal, or gravitational).

Details of the Radial Opposed Migration Classifier

Figure 1B:
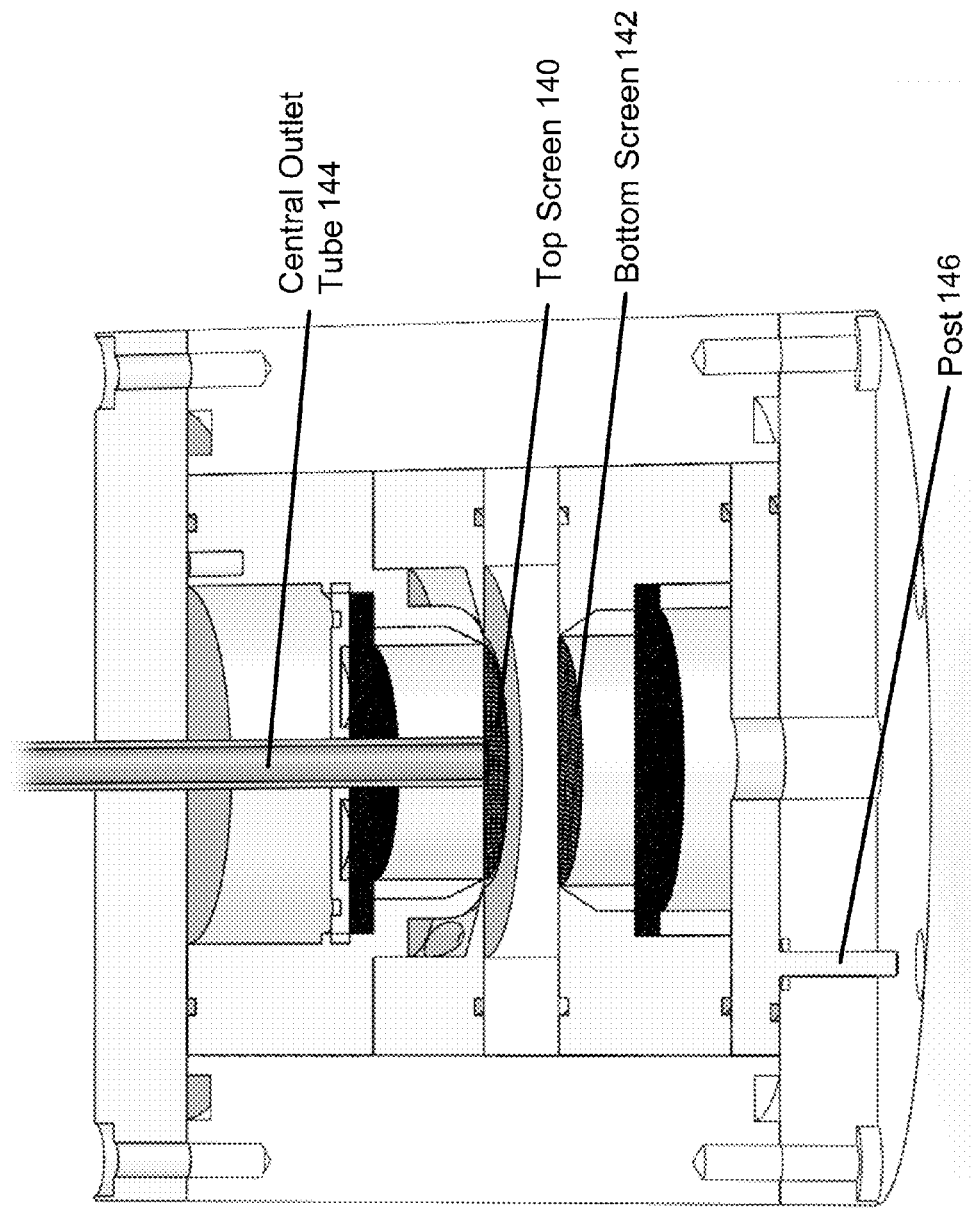
Figure 1C:
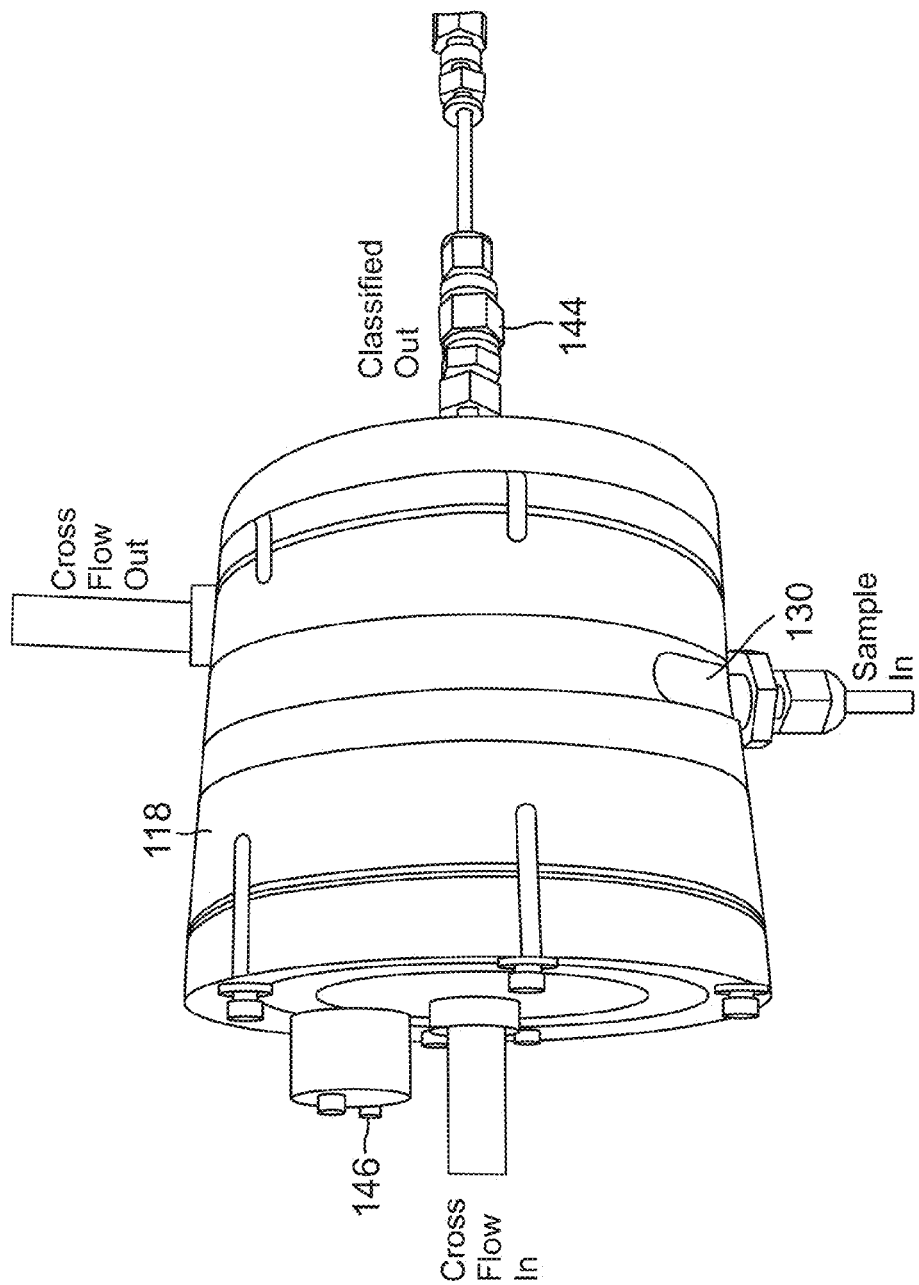

FIGS. 1A-C provide examples of a general structure of a radial opposed migration classifier. FIG. 1A shows a perspective view of a 2-plane sectional cut of an assembled ROMAC system 100 in accordance with one or more embodiments of the invention. A top lid 110, a bottom lid 128, and a side case 118 form an outer enclosure for the system 100. FIG. 1B shows a cross-sectional side view of the assembled ROMAC system 100. FIG. 1C is a photograph of an assembled ROMAC. The modular assembly of the ROMAC allows for fine control of key geometric parameters.

Figure 2:
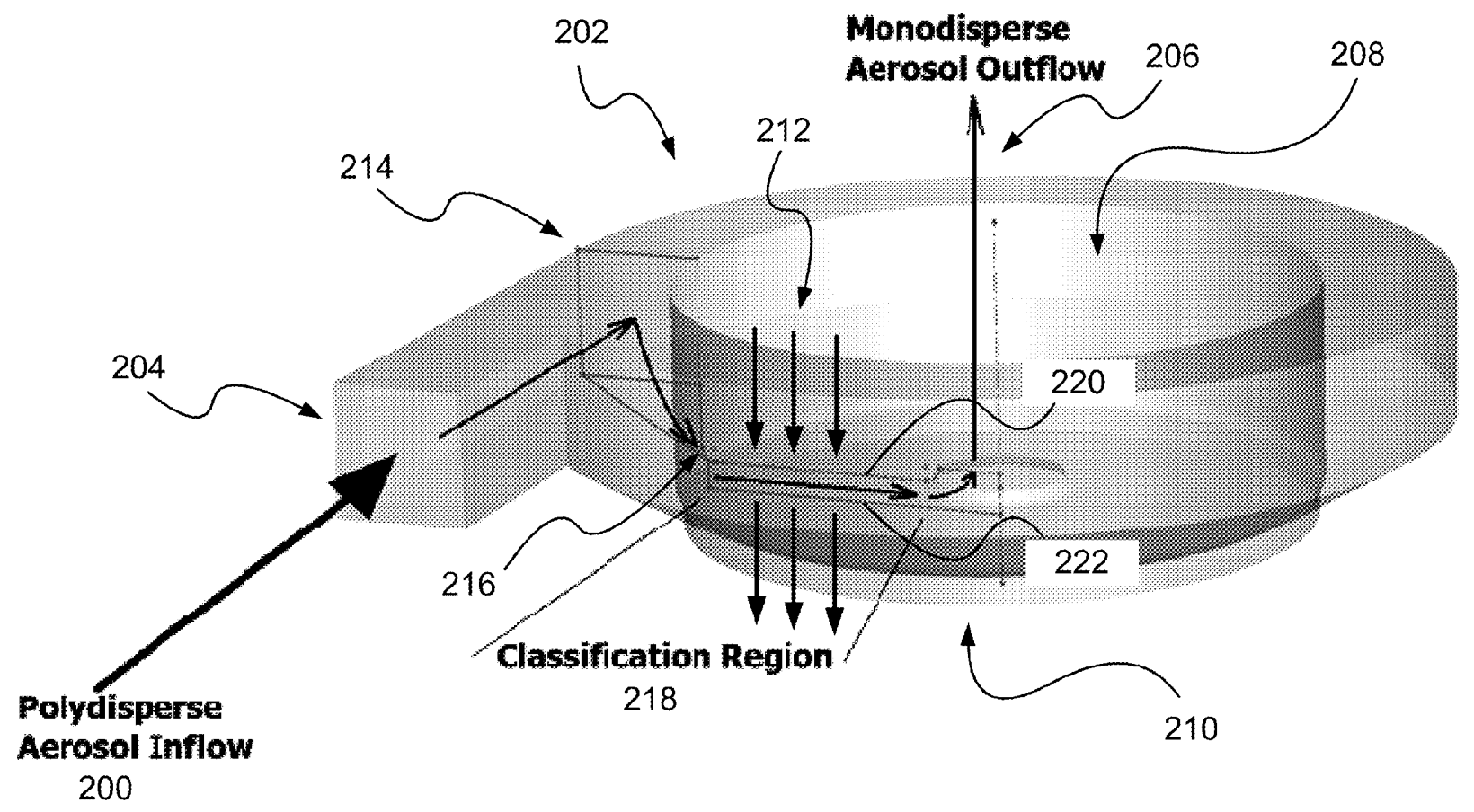
Figure 3:
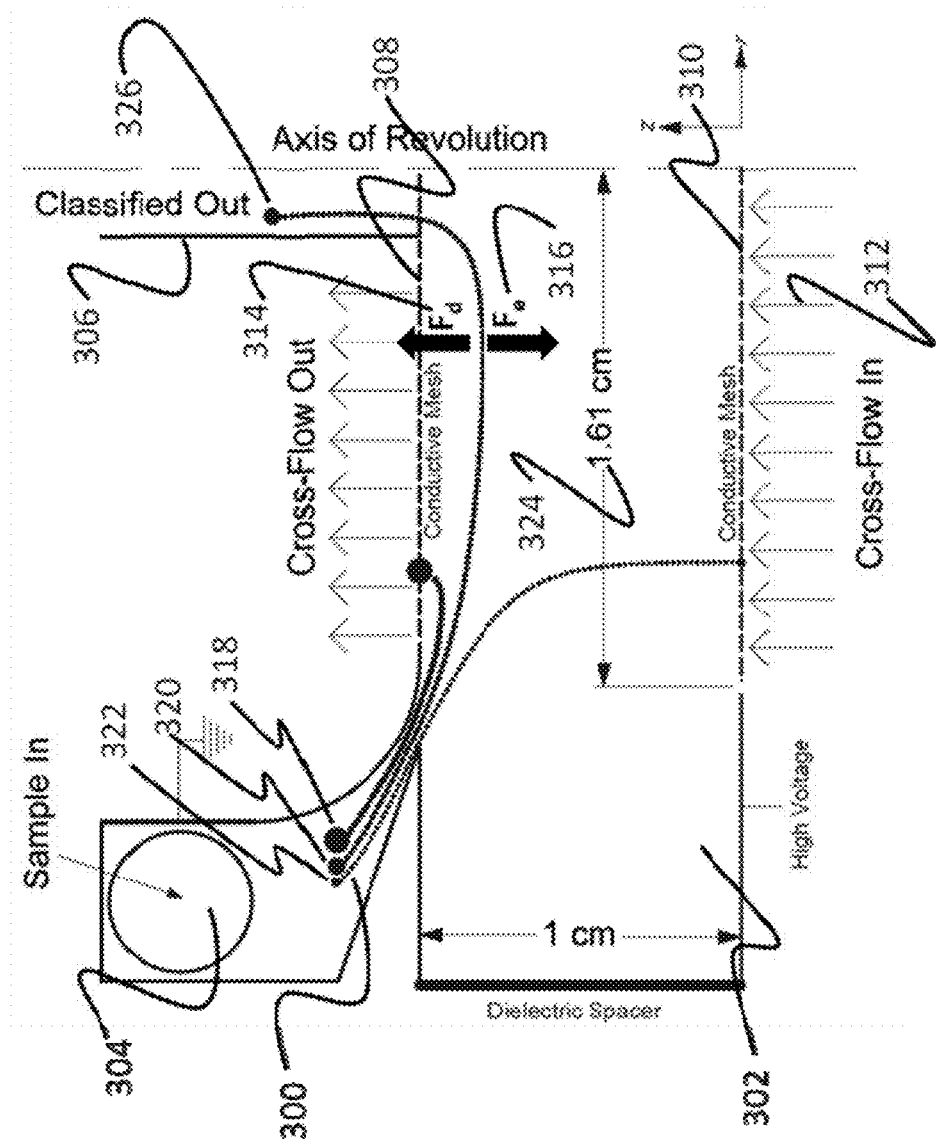
FIG. 3 illustrates a classification region of a radial opposed migration aerosol classifier (ROMAC) in accordance with one or more embodiments of the invention.

A classification region, similar to the classification channel 218 illustrated in FIG. 2 and classification channel 302 illustrated in FIG. 3, is created by a knife edge top 102, knife edge bottom 104, variable gap spacer 106, bottom base 108, and conductive, porous circular screens 140 and 142 respectively stretched across top screen holder 116 and bottom screen holder 120. An embroidery hoop-inspired method may be used for stretching a conductive porous screen/electrode. The thickness dimension of variable gap spacer 106 may be adjusted to change the space between the knife edge top 102 and bottom base 108. A top screen holder 116 and a bottom screen holder 120 are used to hold respective top and bottom permeable circular walls/screens 140 and 142, such as stretched stainless steel mesh. A top frit 114 and bottom frit 122 serve to laminarize the cross-flow before it enters the classification region. The top frit 114 is held in place and may be positionally adjusted within the system 100 by a threaded frit spacer 112. Similarly, bottom frit 122 is held in place and may be positionally adjusted within the system 100 by a bottom frit spacer 124.

Additionally, the top frit 114, threaded frit spacer 112, and top lid 110 all include respective central openings 134, 136, and 138 for a central outlet tube 144 to pass through and rest on the circular screen 140 stretched across top screen holder 116. The central outlet tube 144 is connected to the classification region and provides a negative pressure that allows particles that are balanced by both the drag and imposed field forces to be discharged from the system 100 through the central outlet tube 144.

A flow distributor channel 130 includes a narrowing gap 132, similar to the narrow knife gap 216 illustrated in FIG. 2, which leads to the classification region. The narrowing gap 132 is created by the knife edge top 102 and knife edge bottom 104.

In one or more embodiments, top lid 110, knife edge top 102, knife edge bottom 104, top screen holder 116, top frit 114, threaded frit spacer 112, and the outlet tube 144 that passes through central openings 134-138 and rests on the conductive circular screen 140 stretched across top screen holder 116 are at electrical ground. Side case 118, variable gap spacer 106, and bottom lid 128 are electrical insulators. Bottom base 108, bottom screen holder 120, bottom frit 122, bottom frit spacer 124, variable gap compensator spacer 126, and the conductive circular screen 142 stretched across bottom screen holder 120 are at a non-ground electrical potential. A post 146 extends from variable gap compensator spacer 126 through bottom lid 128 and serves as a means to apply a non-ground electric potential.

FIG. 2 is an illustrative diagram of how a sample 200 would traverse the interior sample volume of a ROMAC 202. ROMAC volume 202 has an inlet port 204 and outlet port 206 for a sample 200, such as polydisperse, positively charged aerosol, and an inlet port 208 and outlet port 210 for a vapor-free cross-flow 212. The aerosol inlet port 204 of the ROMAC volume 202 would receive the sample 200, which would enter a flow distributor channel 214 ("racetrack"). Typically, the flow distributor channel 214 forms a ring or "racetrack" that is concentric to the circular walls 220, 222. In one or more embodiments, the sample 200 enters the flow distributor channel 214 tangentially. The tangential introduction of sample 200 to the flow distributor channel 214 reduces particle loss by impaction, as well as assists in uniform sample distribution in a radial manner. Due to the pressure difference between the racetrack 214 and the sample outlet 206, the sample 200 will be uniformly and radially drawn toward the center outlet port 206 through a narrow knife edge gap 216. After passing through the narrow knife edge gap 216, the sample 200 is now in the classification region 218, where only the particles that are balanced by both the drag and imposed field forces imparted on them will successfully traverse the classification region 218 and exit the ROMAC volume 202 through the central outlet port 206.

The aerosol inlet port 204 may be open to ambient fluid or be connected to an apparatus that would provide the sample 200, such as a reaction chamber, electrospray ionization chamber, or nebulizer. The aerosol outlet port 206 may be connected to an apparatus that would provide negative pressure, such as a condensation nuclei counter pulling a vacuum. The cross-flow inlet port 208 may be connected to an apparatus that would provide vapor-free clean air at a controlled temperature and flow rate, while the cross-flow outlet port 210 may be connected to a vacuum that would result in a matched flow rate to the cross-flow inlet 208. In one or more embodiments, the upper circular wall 220 of the classification region is at electrical ground voltage, while the bottom circular wall 222 of the classification region is at a high positive voltage.

Details of the Classification Region of the Radial Opposed Migration Classifier

FIG. 3 is an illustrative diagram of how particles in a fluid sample are separated/classified in the classification region of a radial opposed migration classifier in accordance with one or more embodiments of the present invention. A particulate-laden fluid sample 300 is pumped or injected into a classification channel 302 from a tangential inlet port 304, similar to the aerosol inlet port 204 in FIG. 2. A pressure difference between the inlet/entrance 304 (i.e. where the sample is injected) and outlet/exit 306 (i.e. where the sample is discharged) regions of the classification channel 302 causes the sample 300 to flow in one direction through classification channel 302. The particulate-laden sample 300 may be a polydisperse sample (i.e. comprising particles of various size, shape, and/or mass) or may be a monodisperse sample (i.e. comprising particles of uniform size, shape, and/or mass). FIG. 3 shows, for example, a polydisperse sample 300 comprising particles of various sizes, 318, 320, and 322.

The sample 300 travels between two circular walls 308 and 310 of classification channel 302 that are permeable to the flow of gases or liquids. The permeable circular walls 308 and 310 may include filters that can capture particles or may be made of a mesh, screen, foam, frit, honeycomb, or porous material (e.g., a porous metal such as sintered metal) that allows particles to pass through it.

A fluid cross-flow 312 enters the classification channel 302 through a circular wall 310, and exits through the opposing circular wall 308. The fluid cross-flow 312 may be a gas or liquid and imparts a drag force 314 ($F_d$) on the particles suspended within the sample fluid. The drag force 314 is strong enough to potentially cause all the particles in sample 300 to be lost by passing through the circular wall 308 or by deposition onto the circular wall 308.

In one or more embodiments, the cross-flow 312 is at a desired temperature predetermined by a user. As the cross-flow fluid 312 replaces the sample fluid by forcing the sample fluid out of the channel 302 through the opposing wall 308, the predetermined temperature of the cross-flow 312 rapidly replaces and changes the temperature of the sample and its particles.

In one or more further embodiments, the cross-flow 312 is vapor-less. By forcing the sample fluid out of the channel 302 through opposing wall 308, a sample fluid that includes trace vapors is replaced with a cross-flow fluid 312 that is vapor-less. Thus, any trace vapors that are introduced when the sample 300 is injected into the channel 302 are removed/replaced with the vapor-less cross-flow.

Additionally, an imposed field imparts a force 316 counter to the drag force 314. The imposed field can take several forms. For example, the particles 318-322 may be first charged or may already carry a charge and the imposed field may be an electric field that causes the particles 318-322 to move counter to the cross-flow 312.

Likewise, the imposed field may be a magnetic field that is imposed on magnetic particles. In another example, the classification channel 302 is horizontal or inclined at an angle so that gravitational sedimentation counters an upward cross-flow. The classification channel 302 may also be arranged in a drum and spun so that centrifugal forces are imposed on the particles 318-322. Temperature differences between the two circular walls 308 and 310 may also be used to create a thermophoretic migration of the particles 318-322 that is counter to the cross-flow 312.

In one or more embodiments, as illustrated in FIG. 3, the imposed field is an electric field created by a conductive circular wall 310 at a high voltage and a conductive circular wall 308 at ground voltage. The voltage difference imparts an electric force ($F_e$) 316 on the particles 318-322 in a direction that is counter and opposite to the drag force 314. Depending on certain properties/characteristics of the particles 318-322, such as the size, shape, and/or mass, the electric force 316 will cause each particle 318-322 to migrate at a specific velocity towards circular wall 310.

Due to the advective flow of the sample 300 through classification channel 302, particles 318-322 of a certain property/characteristic (e.g. size, shape, mass, charge) that are substantially balanced by the drag force 314 and the force 316 created by the imposed field will traverse the classification region, while particles 318-322 that are different and subject to unbalanced forces will impact one of the circular walls 308 or 310. In other words, if the cross-flow 312 velocity is exactly equal but opposite to the migration velocity of the particles 318-322 due to the imposed field, the particles 318-322 will remain entrained in the sample and be carried straight though classification channel 302. Particles 318-322 that migrate at a higher or lower velocity than the velocity of the cross-flow 312 are transmitted to one of the circular walls 308 or 310. These particles 318-322 are lost through the circular walls 308/310 or may be disposed of, for example by deposition on and adhesion to the circular walls 308/310.

FIG. 3 illustrates a polydisperse sample 300, comprising particles 318, 320, and 322 of varying sizes that migrate at different velocities, which result in varying mobility separations. By adjusting the cross-flow velocity and the imposed field, a particle of a desired size 320 will remain in the classification channel 302 while the other particles 318 and 322 are removed. Specifically, a smaller particle 322 exits the classification channel 302 through circular wall 310 and a larger particle 318 exits through circular wall 308, while a particle of the desired size 320 exits through the outlet region 306 of classification channel 302. In other embodiments, for example when the imposed field is gravity-based, the respective directions of larger and smaller particles 318 and 322 are opposite of that for an imposed electric field.

Note however, that for the particle 320 to reach the outlet 306 of the classification channel 302, the velocity of the cross flow 312 need not be exactly equal and opposite the particle migration velocity caused by the imposed field. Particles 318-322 subject to slightly unbalanced counteracting velocities may still successfully traverse the classification channel 302 due to the finite length of classification channel 302. Particles 318-322 migrating at a velocity that is sufficiently close to and opposite the cross-flow 312 may possibly remain entrained in the sample 300 for a sufficient amount of time to travel through classification channel 302 and be discharged before impacting circular wall 308 or 310. Thus, the diameter 324 of the classification channel 302 may be changed depending on the desired level of specificity for particles 318-322 of particular properties/characteristics (e.g., size, shape, mass, charge). Successful particle travel through a classification channel 302 with a longer diameter would require more balanced counteracting forces on the particle 318-322, which means a smaller range of variability in the properties/characteristics (e.g., size, shape, mass, charge) of the particles 318-322 discharged. On the other hand, successful particle travel through a classification channel 302 with a shorter diameter would require less balancing of the counteracting forces on the particle 318-322, which means a greater range of variability in the properties/characteristics (e.g., size, shape, mass, charge) of the particles 318-322 discharged.

The sample 300 comprising classified particles 318-322 of a certain property is continuously discharged from classification channel 302 as a classified sample flow 326. The cross-flow 312 exiting through circular wall 308 or the sample flow 326 exiting the classification channel 302 through outlet 306 may be analyzed or scanned continuously to determine particle property/characteristic (e.g., size, mass, charge) distributions. For example, knowledge of the particle size dependence for migration velocity or mobility and the strength of the cross-flow 312 and the imposed field would enable a determination of the particle size distributions.

In embodiments of the invention, the distribution of particles with respect to the appropriate migration (electrophoretic for charged particles in an electric field, magnetophoretic for magnetic particles in a magnetic field, thermophoretic in the presence of a temperature gradient, sedimentation for gravitational separations) can be determined by stepping either the imposed field strength, or the cross-flow 312 rate through a range of values, and measuring the concentration of particles 318-322 that is transmitted (i.e., particles 318-322 that exit the classification channel 302 in the classified-sample flow 326). Accordingly, the migration for the particles 318-322 in the sample flow may be determined by slowly increasing/decreasing the cross-flow 312 or the imposed field in a stepwise fashion while measuring the particle concentration in the classified-sample flow 326.

In addition, if the particles 318 and 322 are allowed to migrate through the circular walls 308 and 310, provision may be taken to remove the particles 318 and 322 from the cross flow 312 so that the cross-flow 312 can be re-circulated. Such provisions may include filtration of the cross-flow 312 after it exits the classification channel 302.

Logical Flow

Figure 4:
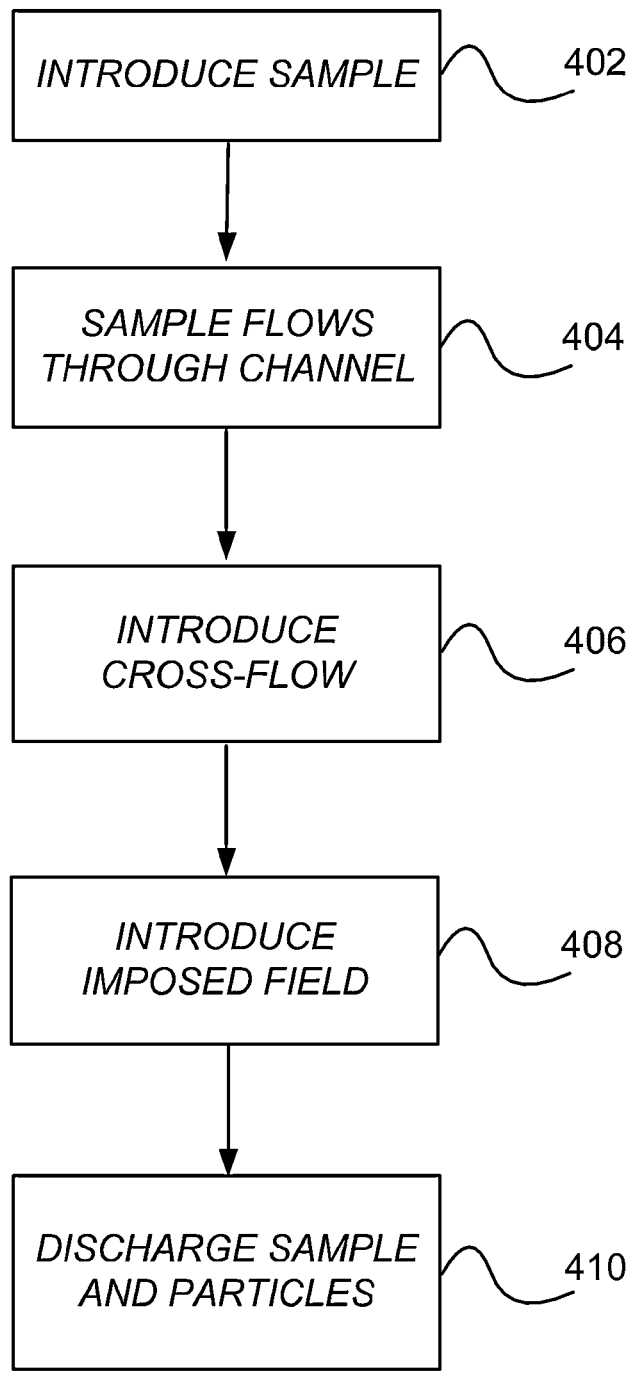
FIG. 4 is a flow chart illustrating a logical flow for separating/classifying particles in a fluid sample in accordance with one or more embodiments of the invention.
Figure 5:
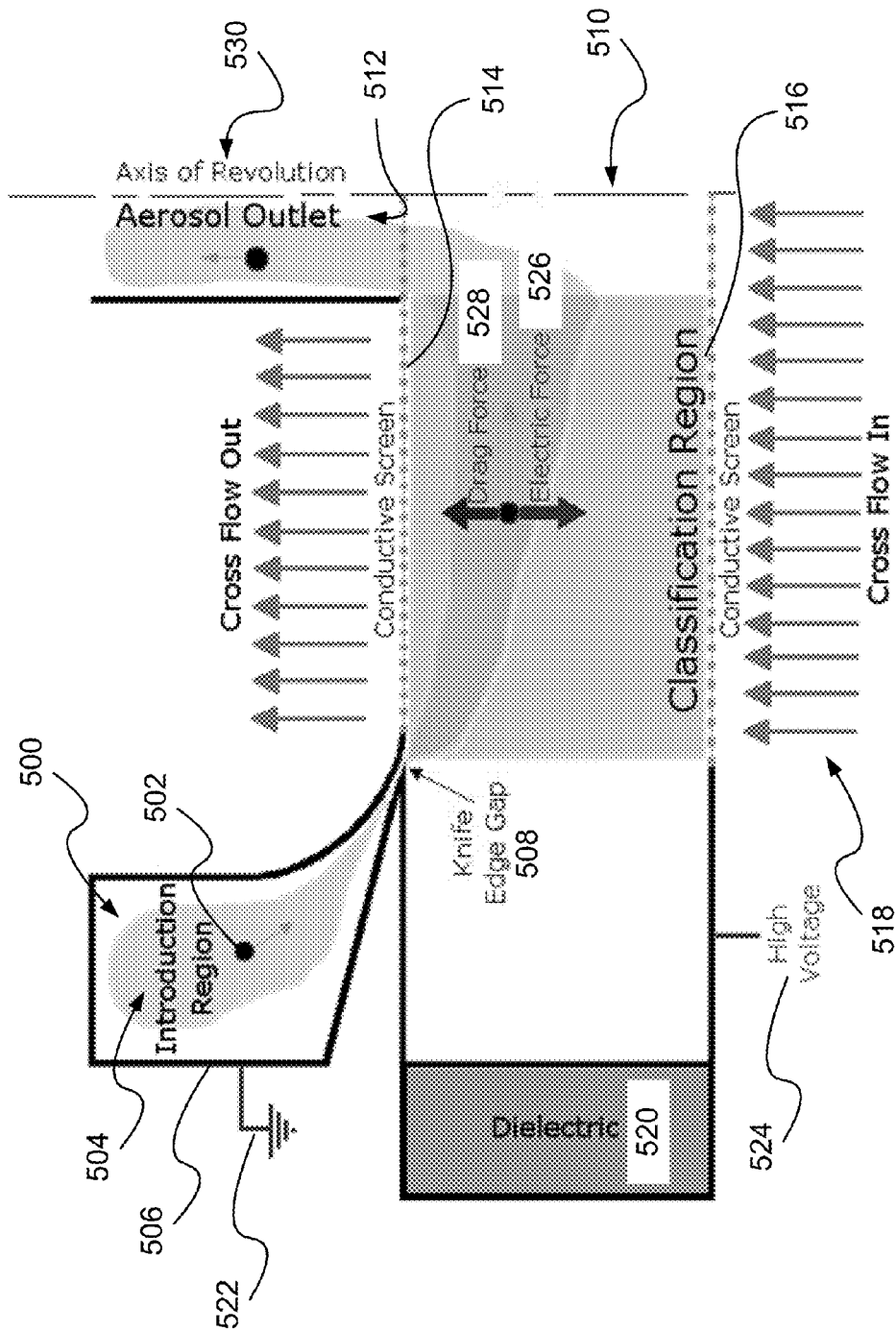
FIG. 5 illustrates a radial opposed migration aerosol classifier (ROMAC) in accordance with one or more embodiments of the invention.

FIG. 4 is a flow chart illustrating a logical flow 400 for separating/classifying particles in a fluid sample in accordance with one or more embodiments of the invention as shown in FIG. 5. At block 402, a sample 500, comprising one or more particles 502 suspended within a sample fluid 504, is introduced into a flow distributor channel 506 which subsequently introduces the sample 500 into a classification channel 510. The sample 500 may be a variety of substances in a variety of forms. For example, the sample 500 may take the form of an aerosol, gas mixture, colloid, suspension of particles in a fluid, or liquid solution. Furthermore, the sample 500 may be a polydisperse sample (i.e. comprising particles of various size, shape, and/or mass) or may be a monodisperse sample (i.e. comprising particles of uniform size, shape, and/or mass). The sample 500 may also include trace vapors that are also introduced when the sample 500 is introduced (e.g. injected or pumped) into the flow distributor 506 and/or classification channel 510.

An inlet port first receives the sample 500, which then enters the flow distributor channel 506. In one or more embodiments, the sample 500 is introduced tangentially into the flow distributor channel 506. In one or more further embodiments, the flow distributor channel 506 comprises a narrowing gap 508 leading into the classification channel 510. Due to a pressure difference between the flow distributor channel 506 and the sample outlet 512, the sample 500 is uniformly drawn and/or pushed from the flow distributor channel 506 into the classification channel 510 through the narrowing gap 508.

At block 404, the sample 500 is introduced to the classification channel 510 through the flow distributor channel 506 and flows through the classification channel 510. The classification channel 510 has a first circular wall 514 and a second circular wall 516 that are both permeable to a flow of fluid (liquid or gas). The pressure difference between the inlet/entrance region (i.e. where the sample 500 is introduced by the flow distributor channel) and outlet/exit region (i.e. central outlet port 512 where the sample 500 is discharged) of the classification channel 510 causes the sample 500 to flow in one general direction through the classification channel 510 (i.e. radially drawn towards the center or axis of revolution 530 of the permeable circular walls 514 and 516). In one or more embodiments the sample flow is laminar. In one or more other embodiments, the classification channel 510 is part of a classification region of a radial opposed migration aerosol classifier (ROMAC).

At block 406, a cross-flow fluid 518 is introduced to the classification channel 510 through one of the permeable circular walls 516. This results in a drag force 528 on the sample 500 and particles 502. The cross-flow 518 may also be a variety of substances in a variety of forms. For example, the cross-flow 518 may be a liquid, gas, or comprise solids suspended in a fluid, etc. The cross-flow 518 flows at a first velocity and exits in a first direction through the other permeable circular wall 514. In one or more embodiments, a top frit 114 and/or a bottom frit 122 respectively above and below the first and second permeable circular walls 514, 516 are used to laminarize the cross-flow 518 before it enters the classification channel 510.

At block 408, an imposed field is applied in a second direction that is counter to the first direction of the cross-flow 518. In one or more embodiments, the direction of the imposed field is orthogonal to the direction of the flow of the sample particles 502 through classification channel 510. The imposed field causes the targeted particles 502 in the sample to migrate at a velocity that is opposite and/or equal in magnitude to the velocity of the cross-flow 518. Therefore, as the cross-flow 518 forces the sample fluid 504 to exit along with it through the permeable circular wall 514, the particles 502 that are balanced by the imposed field and cross-flow 518 remain within the classification channel 510 and are retained in the sample 500. For particles where the imposed field subjects a force that is not equal to the cross-flow, the particles will move in an overall direction towards one of the permeable circular walls 514, 516 rather than remain between the circular walls 514, 516. In one or more embodiments, as shown in FIG. 5, a dielectric 520 creates an electric potential by having the conductive circular wall 514 be at electrical ground voltage 522 and conductive circular wall be at a high voltage 524. This results in an electric force 526 on the particles 502.

At block 410, the particles 502 remaining in the classification channel 510 (i.e., those particles whose field migration velocity is opposite and equal to the cross-flow velocity) are discharged through the central outlet port 512. It should be noted that the particles 502 may migrate within a range of migration velocities that may not be exactly equal to the cross-flow 518 but still travel through the classification channel 510 and be discharged.

Subsequent actions may then process and/or use the discharged particles 502. In one or more embodiments, the discharged particles 502 may be collected as a classified and/or purified sample. In one or more other embodiments, the discharged particles 502 that travel through the classification channel 510 are classified based on a property of the discharged particles 502, for example a size, mass or charge of the discharged particles 502.

While particles 502 that remain in the flow through the classification channel 510 are discharged, various other particles may be removed from the flow. For example, particles that reach the permeable walls 514, 516 may be removed from the flow through the classification channel 510 either by deposition on and adhesion to the walls 514, 516 or by passing through the walls 514, 516.

It should be noted that the functions noted in the blocks may occur out of the order noted in FIG. 4. For example, in one or more embodiments, blocks 406 and 408 which are shown in succession may in fact occur concurrently/in parallel. In other embodiments, due to the positioning of the cross-flow 518, blocks 406 and 408 may occur in the reverse order, where the particles 502 are subject to the imposed field before coming into contact with the cross-flow 518.

Illustrative Models and Simulations

Figure 6:
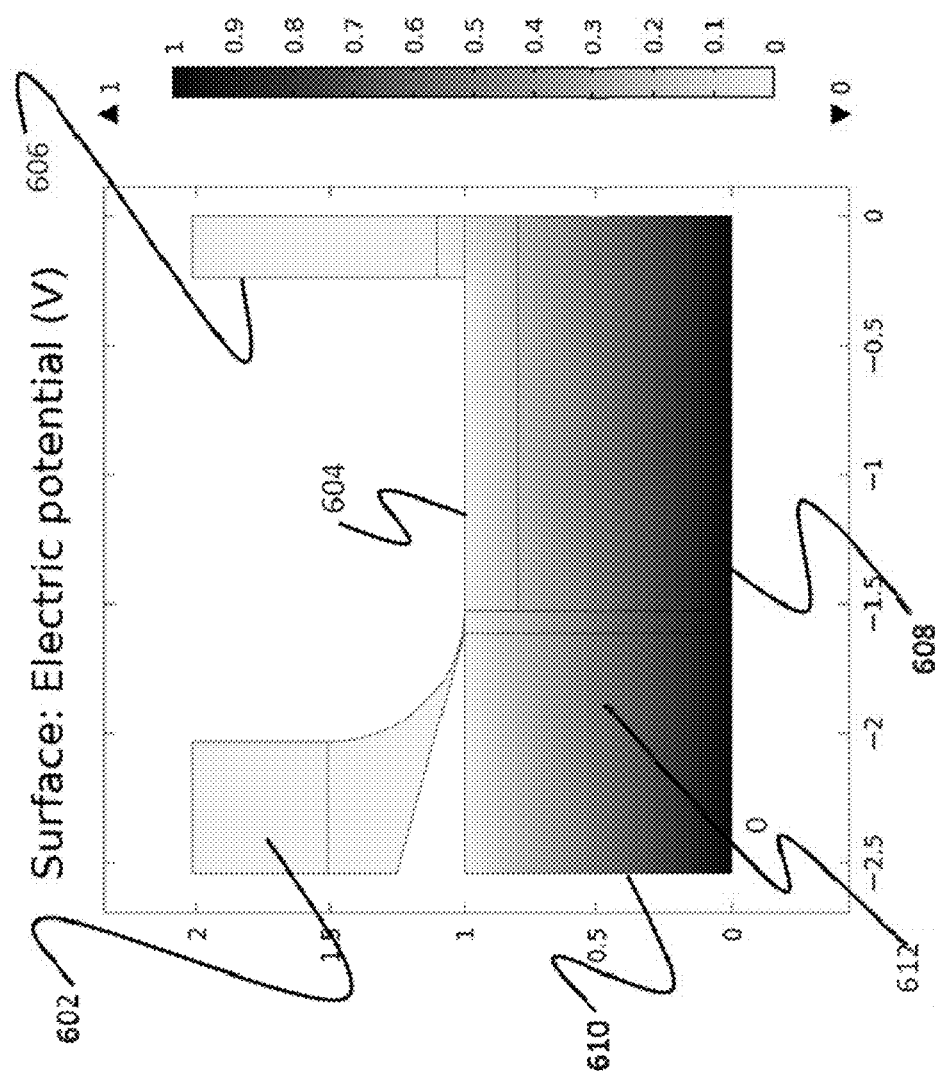
FIG. 6 illustrates an electric potential field distribution model of a solution flowing through a section of a radial opposed migration aerosol classifier (ROMAC) in accordance with one or more embodiments of the invention.
Figure 7:
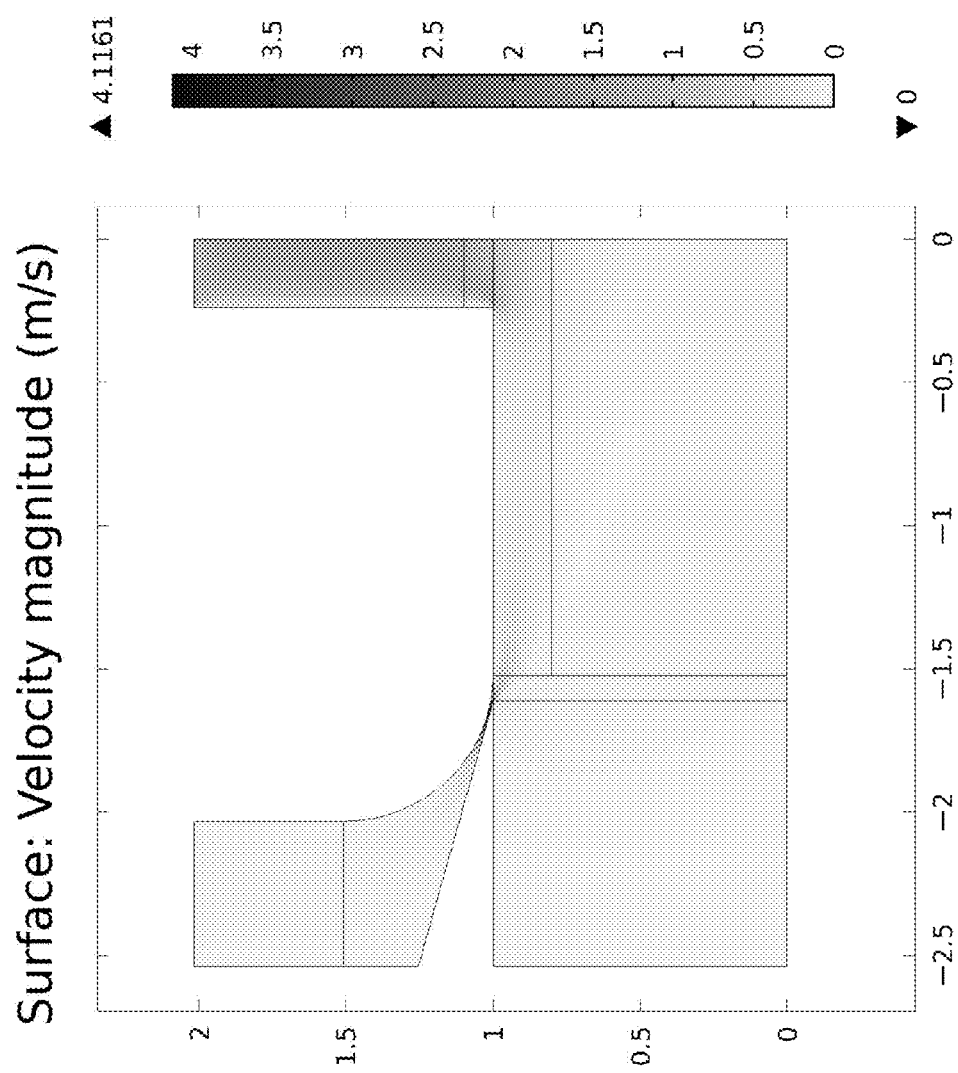
FIG. 7 illustrates a fluid velocity field distribution model of a solution flowing through a section of a radial opposed migration aerosol classifier (OMAC) in accordance with one or more embodiments of the invention.

As illustrative examples, the invention was modeled as a radially symmetric space similar to the ROMAC 202 depicted in FIG. 2 in COMSOL™ Multiphysics 4.1™ to obtain values for fluid properties, fluid flows, and electric fields in the region of the ROMAC through which aerosol particles will flow through. The electric potential solution is shown in FIG. 6 and the combined sample and cross-flow fluid velocity magnitude solution is shown in FIG. 7. More specifically, FIG. 6 illustrates that the introduction region 602, similar to flow distributor channel 506 in FIG. 5, wall 604, similar to permeable circular wall 514 in FIG. 5, and outlet 606, similar to central outlet port 512 in FIG. 5, are at ground potential, while wall 608, similar to permeable circular wall 516 in FIG. 5, is at some non-ground potential. Wall 610 represents a dielectric spacer, similar to dielectric 520 in FIG. 5, which separates walls 604 and 608, allowing for a potential field to exist in classification region 612, similar to classification region 510 in FIG. 5. Additionally, FIG. 7 shows that the high flow velocity regions are in the knife edge gap and sample outlet, similar to knife edge gap 508 and sample outlet 512, respectively, in FIG. 5. This is due to a pressure difference between sample outlet 512 and flow distributor channel 506 that draws the sample from the flow distributor channel 506 toward the sample outlet 512. The sample thus flows radially inward toward the sample outlet 512, in a direction that is orthogonal to the potential field in FIG. 6.

The COMSOL™ solutions were then used as inputs for a MATLAB™ script developed to simulate the trajectories of particles of a particular size when released into the ROMAC aerosol space. The trajectories used inputs of fluid velocity, density, viscosity, temperature, and electric potential to simulate the movement of particles in finite time steps. In addition, the diffusional movement of the particles was simulated as well.

Figure 8:
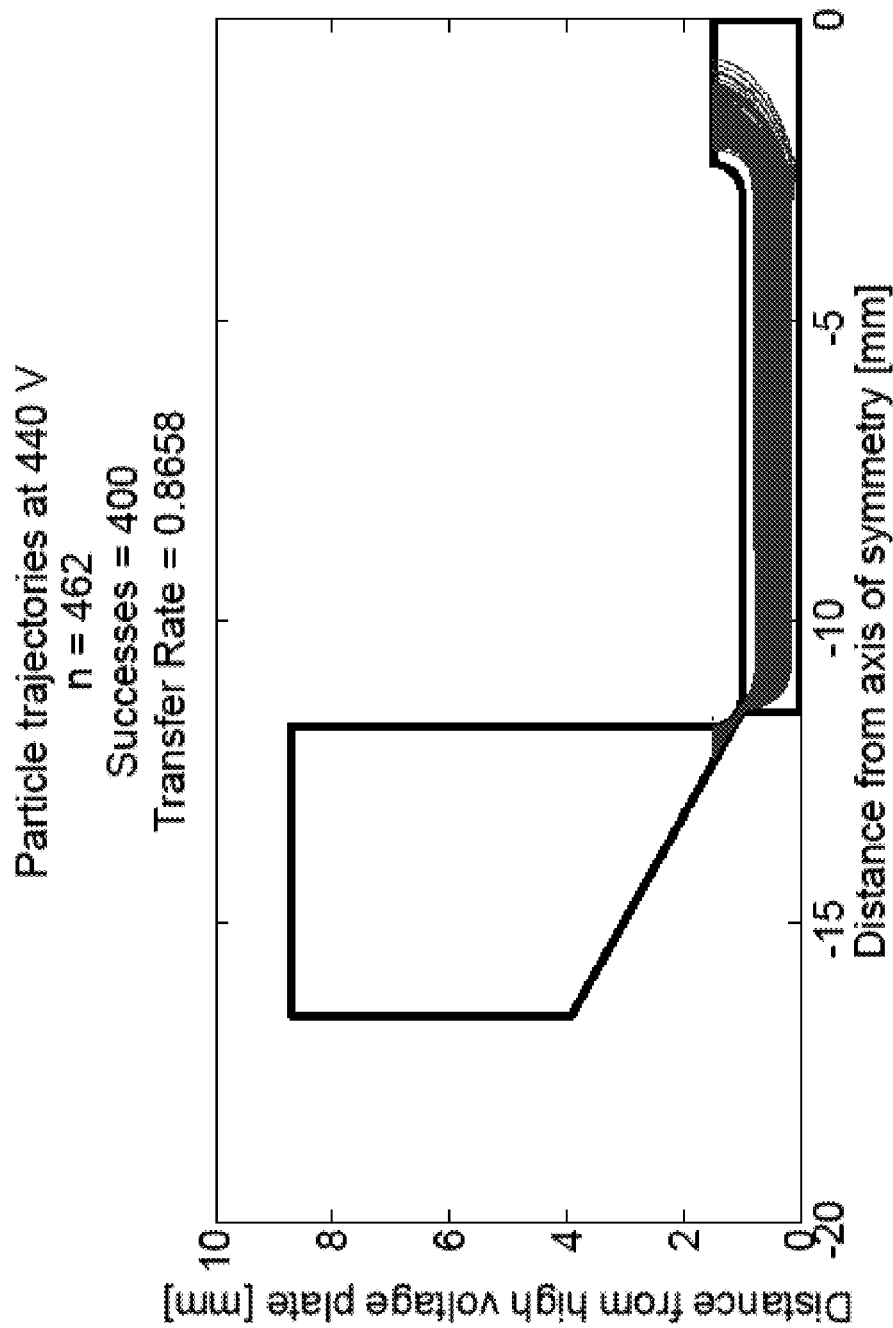
FIG. 8 illustrates a particle trajectories simulation model of a solution flowing through a section of a radial opposed migration aerosol classifier (ROMAC) in accordance with one or more embodiments of the invention.

FIG. 8 illustrates a simulation of 100 nm particles traversing the ROMAC at a voltage that was predicted to yield the maximum transmission of particles through the classification region. The aerosol flowrate was set at 0.1 lpm, cross-flow rate at 0.3 lpm, temperature at 298 K, and voltage at 440 V. The results demonstrate the feasibility of the invention, as the numerical simulations were executed with well-reputed software and relied on the established knowledge of mechanisms of particle movement. In addition, FIG. 8 demonstrates that the use of a sample inlet and outlet at the same electric potential greatly reduces particle losses, since 400 out of 462, or 87%, simulated particles were transmitted through the ROMAC. FIG. 8 shows a reduction of particle diffusion to the walls of the classification region that would otherwise result from unfavorable voltage transitions that occur in nearly all other DMA designs.

Figure 9:
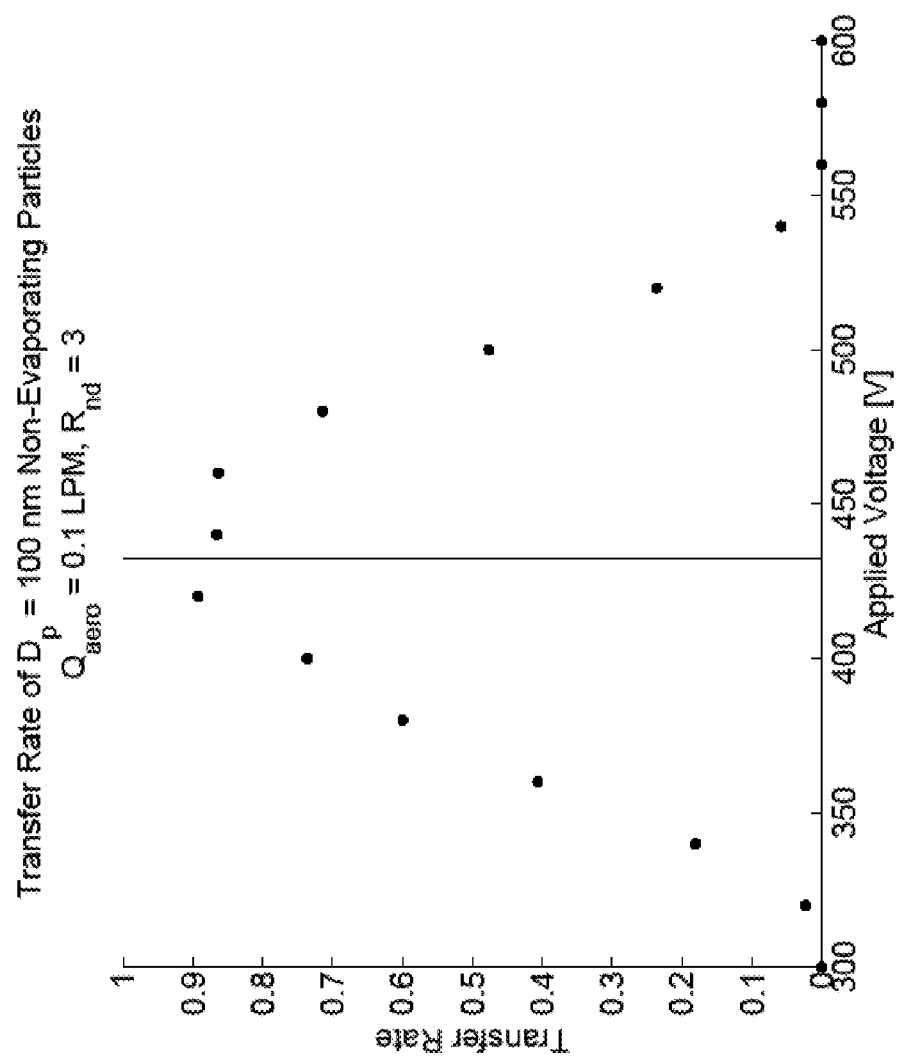
FIG. 9 illustrates a particle transfer simulation model of a solution flowing through a section of a radial opposed migration aerosol classifier (ROMAC) in accordance with one or more embodiments of the invention.

The type of simulation illustrated in FIG. 8 was repeated at various voltages to obtain a predicted transfer function (FIG. 9) for the ROMAC in the case of 100 nm particles at an aerosol flow rate of 0.1 lpm, a cross-flow rate of 0.3 lpm, and temperature of 298 K. The vertical line in FIG. 9 is the theoretical voltage that would result in a balance of the drag force and electric force imparted on the particles (which would result in maximum transmission, i.e. 100% transmission of the particles). The peak of the simulated transfer function is in very good agreement with the theoretical voltage for 100% transmission. The resolution of the ROMAC in this simulation is estimated to be roughly 3, which compares favorably to the maximum theoretical non-diffusive resolution of 3. Thus, FIG. 9 also shows that the introduction and extraction of the sample from an inlet and outlet at the same electric potential greatly reduces diffusive particle losses that would otherwise degrade the resolution from the maximum theoretical non-diffusive resolution.

Illustrative Experimental Results and Discussion
Ion Mobility Spectrometry: Exemplary Application of the ROMIAC TSI™ classic DMAs are able to classify particles in the range of 10-1000 nm. Even TSI™ nano-DMAs only have a range of 2-150 nm. Thus, there is a need for a particle classifier that is optimal in the sub-10 nm regime, not just touching it. This is important due to the persistent 1-2 nm cluster mode in the background atmosphere and because particle formation takes place below 3 nm [13].

In an exemplary application, ion mobility spectrometry was performed with a radial opposed migratory ion/aerosol classifier (ROMIAC) to demonstrate the ability of the ROMIAC in separating particles in the sub-10 nm regime. Even though no condensation particle counters (CPC) were available to detect 1 nm particles and no polystyrene latex (PSL) standards were that small, there still existed other size standards (and quasi-standards) that could be detected with a mass-spectrometer, in this instance, tetraalkylammonium halides (TAAX) and peptides.

Figure 10:
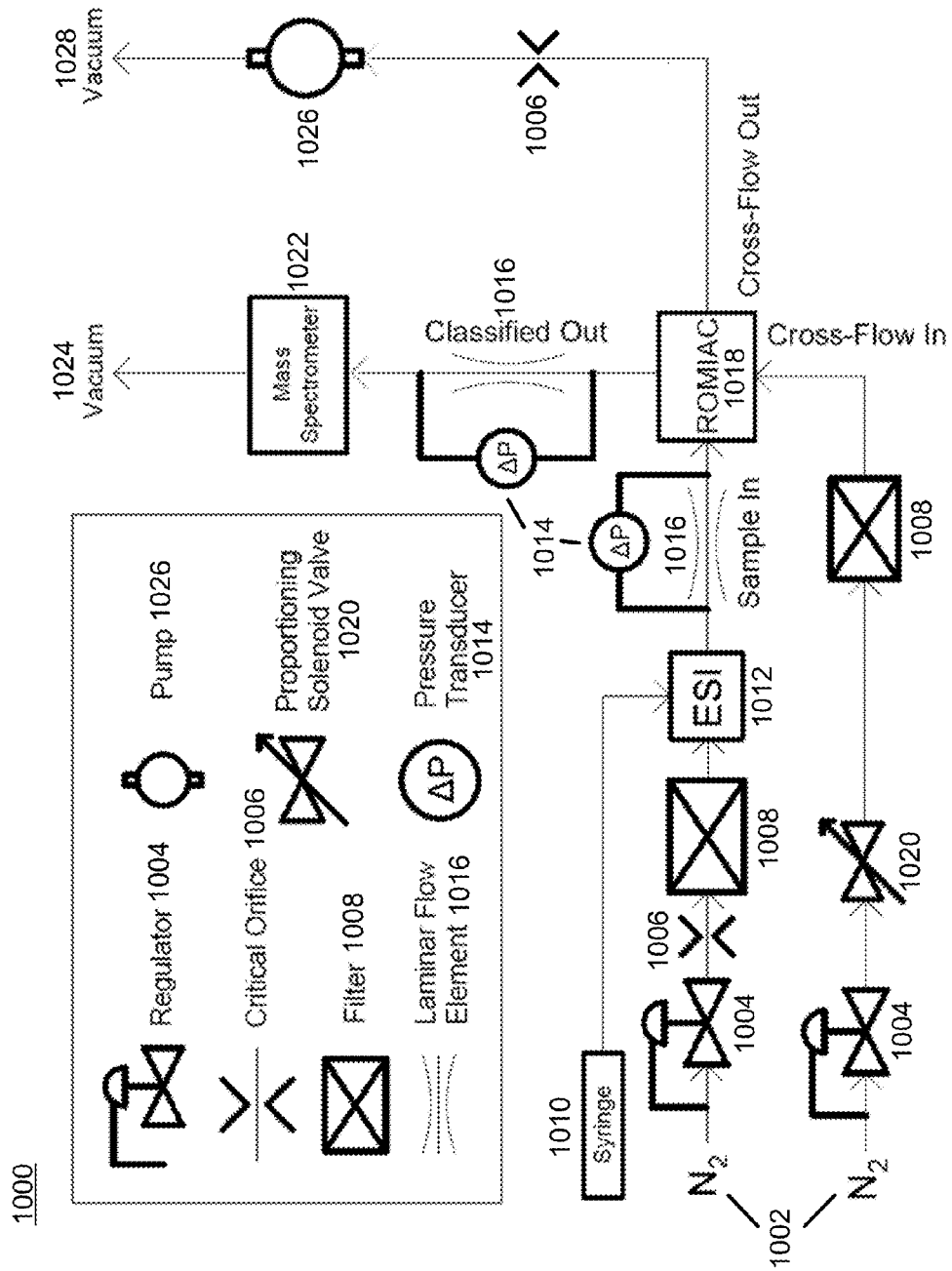
FIG. 10 illustrates a schematic of a system setup using the radial opposed migration ion/aerosol classifier (ROMIAC) for ion mobility-mass spectrometry, in accordance with one or more embodiments of the invention.

FIG. 10 illustrates a schematic of a radial opposed migration ion/aerosol classifier (ROMIAC) system in accordance with one or more embodiments of the invention. More specifically, the schematic of FIG. 10 shows an experimental set-up of a system 1000 used to separate/classify particles.

An inert nitrogen gas 1002 ($N_2$) is used as both the sample fluid and the cross-flow fluid. For the sample fluid, nitrogen gas 1002 passes through a regulator 1004 which has a critical orifice 1006 leading to a filter 1008. The filter 1008 removes any undesired particulates in the nitrogen gas 1002. A syringe 1010 with solution containing the analytes of interest is used to transport the solvated analyte to an electrospray ionization (ESI) spray chamber 1012, which disperses the analyte as a charged, fine aerosol, benefiting from the additional nebulization by the inert nitrogen gas 1002. A pressure transducer 1014 measures the flow rate of the sample aerosol passing through a laminar flow element 1016, where it is then introduced into the ROMIAC 1018. Additionally, inert nitrogen gas 1002 ($N_2$) passes through a regulator 1004 and is controllably released by a proportioning solenoid value 1020. After being filtered by filter 1008, the nitrogen gas 1002 is introduced into the ROMIAC 1018 as the cross-flow.

After the separation process as described above, the desired particles are discharged from the ROMIAC 1018 due to the pressure difference created by vacuum 1024. A pressure transducer 1014 measures the flow rate of the classified aerosol passing through a laminar flow element 1016 prior to being introduced to a mass spectrometer 1022. The cross-flow also exits the ROMIAC 1018 and passes through a critical orifice 1006 where it is pumped by pump 1026 to a vacuum 1028. The flow rates measured by pressure transducers 1014 are balanced by adjusting regulator 1004 until the pressure transducers 1014 report the same flow rate values. Due to critical orifice 1006, it can be assured that the cross-flows entering and exiting ROMIAC 1018 are balanced as well.

As illustrated in FIG. 11, a 2-part calibration was first performed [15]. FIG. 11(a) is a graph depicting the instrument calibration with TAAX [16], which was not affected by ESI solvent contaminants or analyte surface concavities. FIG. 11(a) shows a relatively linear relationship between the peak signal voltage and the inverse mobility of the analyte. FIG. 11(b) is a graph depicting the mobility calibration with peptides [17,18], which was affected by ESI solvent contaminants or analyte surface concavities. FIG. 11(b) shows a relatively linear relationship between collisional cross-section and a relational coefficient β (which is a grouping of variables relating to analyte mass, charge, and temperature in the Mason-Schamp equation).

FIG. 12 is a table detailing the mobility of various TAAX multimers, which are singly-charged anion-coordinated multimers. Generally, as more monomer units are added to a TAAX ion, the cross section increases and the mobility of the TAAX multimer decreases. The superscript is defined as follows: $^a$In N$_2$ at atmospheric pressure and T$_{ESI}$=T$_x$=298 K. Values are the average of three scans. Note that C3 species are iodinated while all other TAAX species are brominated.

Figure 13:
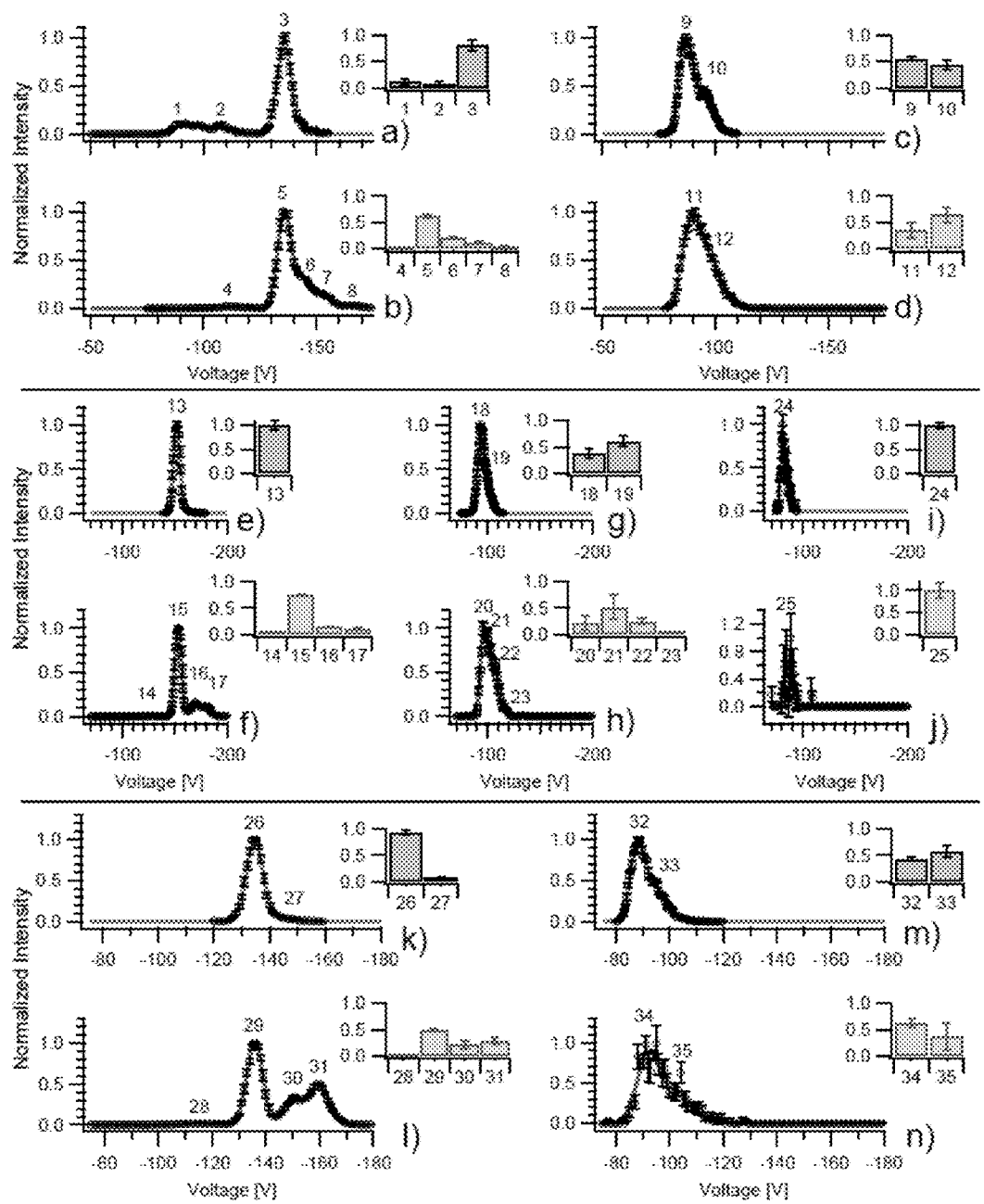
FIGS. 13(a)-(n) are a series of graphs showing the detection of bradykinin, angiotensin I, and angiotensin II at various electrospray ionization chamber carrier gas temperatures (i.e. 298K and 400K) and charge states (i.e. +1, +2, +3)
Figure 14:
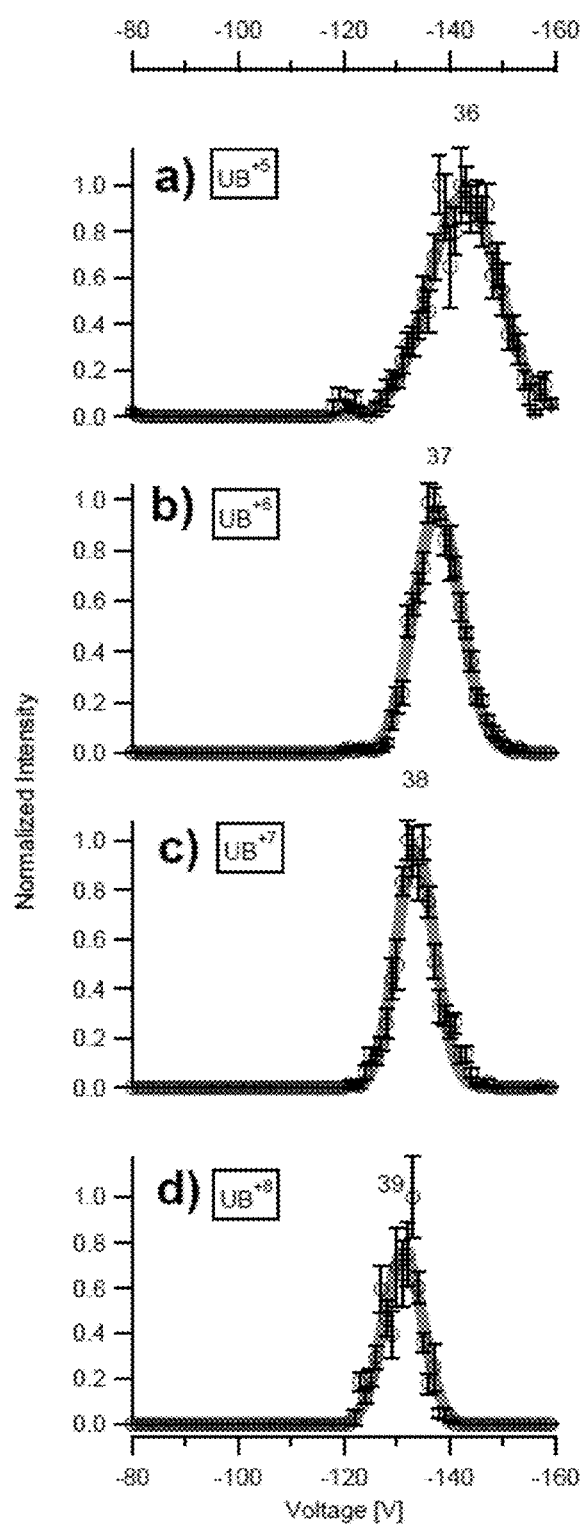
FIGS. 14(a)-(d) are a series of graphs showing the detection of bovine ubiquitin at various charge states (i.e. +5, +6, +7, +8)

FIG. 13 contains graphs illustrating the detection by mass spectrometry of various peptides separated by the ROMIAC. The vertical axis for the graphs represents the normalized intensity of the signal from a mass spectrometer and the horizontal axis for the graphs represents the applied voltage. FIGS. 13(a)-(d) are a series of graphs showing the detection of bradykinin at various temperatures (i.e. 298K (FIGS. 13(a), 13(c)) and 400K (FIGS. 13(b), 13(d))) and charge states (i.e. +1 (FIGS. 13(a)-(b)), +2 (FIGS. 13(c)-(d))). FIGS. 13(e)-(j) are a series of graphs showing the detection of angiotensin I at various temperatures (i.e. 298K (FIGS. 13(e), 13(g), 13(i)) and 400K (FIGS. 13(f), 13(h), 13(j))) and charge states (i.e. +1 (FIGS. 13(e)-(f)), +2 (FIGS. 13(g)-(h)), +3 (FIGS. 13(i)-(j))). FIGS. 13(k)-(n) are a series of graphs showing the detection of angiotensin II at various temperatures (i.e. 298K (FIGS. 13(k), 13(m)) and 400K (FIGS. 13(l), 13(n))) and charge states (i.e. +1 (FIGS. 13(k)-(l)), +2 (FIGS. 13(m)-(n))). FIG. 14(a)-(d) are a series of graphs showing the detection of bovine ubiquitin at various charge states (i.e. +5, +6, +7, +8).

FIG. 15 is a table illustrating the collisional cross-sections, $\Omega_i$, from the two different calibrations, as well as the comparison of the mobility calibration to literature values of the various peptides, bradykinin (BK), angiotensin I (AT1), angiotension II (AT2), and bovine ubiquitin (UB). The superscripts are defined as follows: $^a$In N$_2$ at atmospheric pressure and T$_x$=298 K. Values are the average of three scans; *T$_{ESI}$=298 K; #T$_{ESI}$=400 K; &Peak was used for mobility calibration; $^b$Cross section estimated from instrument calibration (using TAAX ions); $^c$Cross section estimated from mobility calibration (using peptides and proteins); and $^{d,\ e,\ f}$Percent difference between this study's mobility calibration $\Omega_i$ value and that published in [17-19].

Model Peptide Isomer Separation

In an exemplary application, a radial opposed migratory ion/aerosol classifier (ROMIAC) was used to see if model peptides whose sequences differed by only one pair switch could be separated. In this instance, the sequences tested were AARAAATAA vs. AATAAARAA and AARAAHAMA vs. AARAAMAHA. Additionally, a TEMPO tag (2,2,6,6-Tetramethylpiperidin-1-yl)oxyl) was added to see if the tag would modify the structures of the sequences to enhance separation by the ROMIAC.

Figure 16:
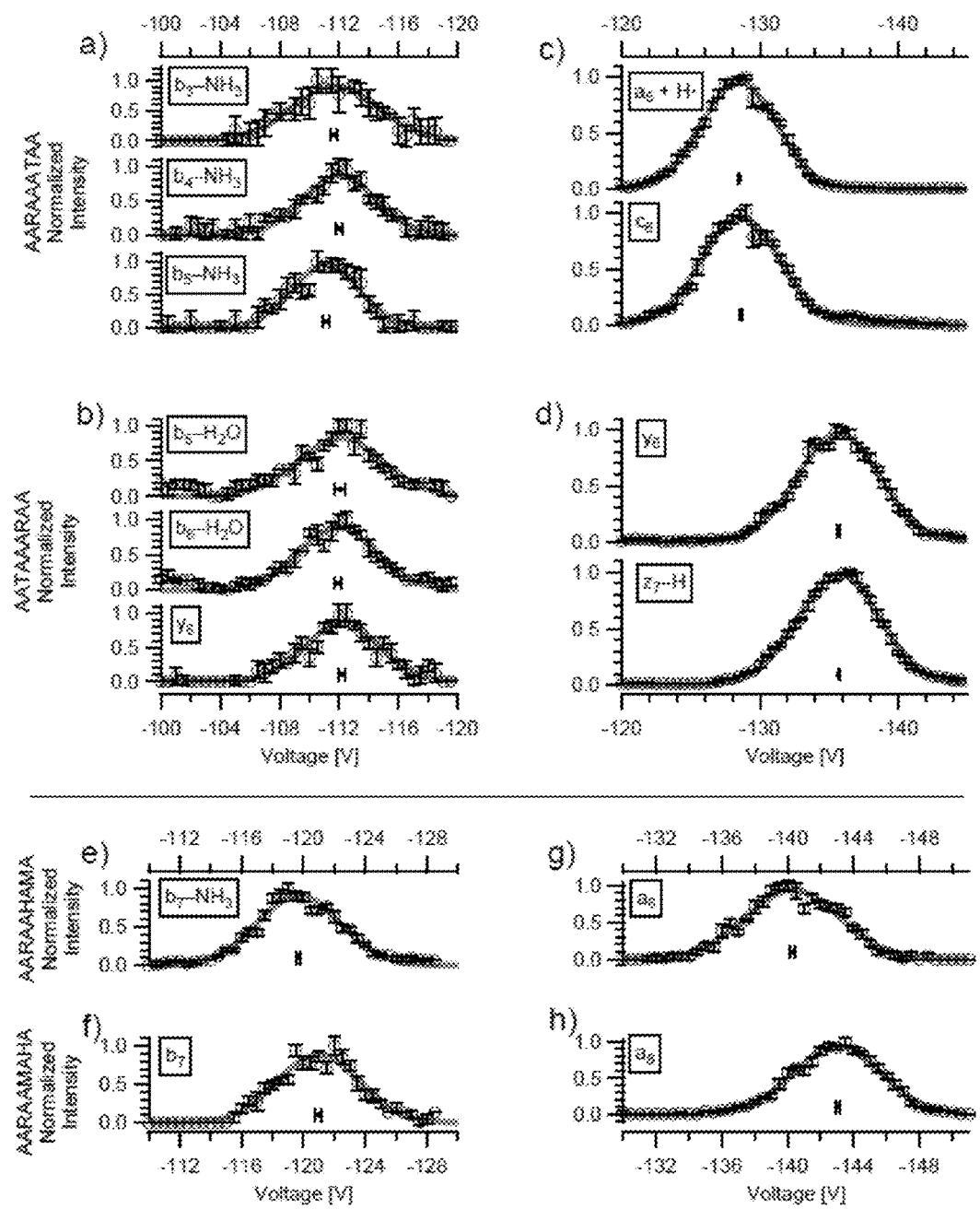
FIGS. 16(a-b, e-f) shows the separation with no 2,2,6,6-Tetramethylpiperidin-1-yl)oxyl (TEMPO) tag attached.

FIGS. 16(a)-(d) illustrate the detection by mass spectrometry of model peptides AARAAATAA vs. AATAAARAA as separated by the ROMIAC. FIG. 16(a)-(b) shows the separation with no TEMPO tag attached. FIG. 16(c)-(d) shows the separation with TEMPO tagged on the peptides. Similarly, FIGS. 16(e)-(h) illustrate the detection by mass spectrometry of model peptides AARAAHAMA vs. AARAAMAHA as separated by the ROMIAC. FIG. 16(e)-(f) shows the separation with no TEMPO tag attached. FIG. 16(g)-(h) shows the separation with TEMPO tagged on the peptides.

These results demonstrate ROMIAC's ability to classify ions/particles. Ions and peptides were successfully classified at the 1-2 nm size range. Resolutions achieved were close to the maximum theoretical resolution based on flow rate ratios (~20). There was also a very linear response in mobility to voltage changes. Furthermore, ROMIAC was able to resolve isomers with small structural differences.

Conclusion

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. All publications, patents, and patent applications cited herein are hereby incorporated by reference in their entirety for all purposes.

REFERENCES

[1] Knutson, E. and K. Whitby, Aerosol classification by electric mobility: apparatus, theory, and applications, *J Aerosol Sci*, 1975, p. 443-451.

[2] Winklmayr, W., et al. A New Electromobility Spectrometer for the Measurement of Aerosol Size Distributions in the Size Range from 1 to 1000 nm. *J Aerosol Sci*, 1991, 22(3): p. 289-296.

[3] Chen, D., et al. Design and Evaluation of a Nanometer Aerosol Differential Mobility Analyzer (Nano-DMA). *J. Aerosol Sci*, 1998, 29(5-6): p. 497-509.

[4] de Juan, L. and J. de la Mora, High Resolution Size Analysis of Nanoparticles and Ions: Running a Vienna DMA of Near Optimal Length at Reynolds Numbers Up to 5000. *J Aerosol Sci*, 1998, 29(5-6): p. 617-626.

[5] Flagan, R. C., Cross-flow Differential Migration Classifier, U.S. Pat. No. 6,905,029.

[6] Zhang, S., et al., Radial Differential Mobility Analyzer. *Aerosol Science and Technology*, 1995, 23(3): p. 357-372.

[7] Zhang, S, and R. Flagan, Resolution of the Radial Differential Mobility Analyzer for Ultrafine Particles. *J Aerosol Sci*, 1996, 27(8): p. 1179-1200.

[8] Brunelli, N. A., R. C. Flagan, and K. P. Giapis, Radial Differential Mobility Analyzer for One Nanometer Particle Classification. *Aerosol Science and Technology*, 2009, 43(1): p. 53-59.

[9] Flagan, R. C. and S. H. Zhang, Radial Differential Mobility Analyzer, U.S. Pat. No. 5,606,112.

[10] Martinez-Lozano, P., M. Labowsky, and J. F. de la Mora, Experimental Tests of a Nano-DMA with No Voltage Change Between Aerosol Inlet and Outlet Slits. *J Aerosol Sci*, 2006, 37(11): p. 1629-1642.

[11] Tammet, H., Symmetric Inclined Grid Mobility Analyzer for the Measurement of Charged Clusters and Fine Nanoparticles in Atmospheric Air. *Aerosol Science and Technology*, 2011, p. 468-479.

[12] Downard, A., J. Dama, and R. Flagan, An Asymptotic Analysis of Differential Electrical Mobility Classifiers. *Aerosol Science and Technology*, 2011, p. 717-729.

[13] Kulmala, M. et al. Toward Direct Measurement of Atmospheric Nucleation. *Science*, 2007.

[14] Flagan, R C. Opposed Migration Aerosol Classifier (OMAC). *Aerosol Science and Technology*, 2004, 38:890-899.

[15] Fernandez-Maestre, R., et al. Chemical Standards in Ion Mobility Spectrometry. *The Analyst*, 2010.

[16] Viidanoja, J., et al. Tetraalkylammonium Halides as Chemical Standards for Positive Electrospray Ionization with Ion Mobility Spectrometry/Mass Spectrometry. *RCMS*, 2005.

[17] Bush, M., et al. Collision Cross Sections of Proteins and Their Complexes: A Calibration Framework and Database for Gas-Phase Structural Biology. *Anal. Chem.*, 2010, 82(22)9557-65;

[18] Wu., C., et al. Atmospheric Pressure Ion Mobility Spectrometry of Protonated and Sodiated Peptides. *RCMS*, 1999, 13(12):1138-42.

[19] Baykut, G., O. von Halem, and O. Raether. Applying a Dynamic Method to the Measurement of Ion Mobility. *Journal of the American Society for Mass Spectrometry*, 2009, 20(11):2070-81.

What is claimed is:

1. A radial opposed migration classifier comprising:
   a classification channel through which passes a sample comprising one or more particles suspended within a sample fluid, the classification channel comprising a first circular wall and a second circular wall that are both permeable to a flow of fluid;
   a flow distributor channel for introducing the sample into the classification channel wherein the flow distributor channel comprises a narrowing gap leading into the classification channel;
   a cross-flow fluid that enters the classification channel through one of the permeable circular walls, wherein the cross-flow fluid flows at a first velocity and exits in a first direction through the other permeable circular wall;
   an imposed field that is applied on the one or more particles in a second direction counter to the first direction of the cross-flow fluid, wherein the imposed field causes the one or more of the particles to migrate at a second velocity opposite and/or equal to a first velocity of the cross-flow fluid; and
   wherein the particles that travel through the channel are discharged from the radial opposed migration classifier.

2. The radial opposed migration classifier of claim 1, wherein the sample is introduced tangentially into the flow distributor channel.

3. The radial opposed migration classifier of claim 1, wherein the flow distributor channel introduces the sample into the classification channel through a same plane as the first circular wall and further wherein the particles that travel through the channel are discharged through a central outlet on the same plane as the first circular wall.

4. The radial opposed migration classifier of claim 1, wherein the imposed field is an electric field.

5. The radial opposed migration classifier of claim 4, wherein the particles are introduced into the classification channel at an electric potential and discharged from the radial opposed migration classifier at the same electric potential.

6. The radial opposed migration classifier of claim 4, wherein the particles are discharged at an electrical ground voltage.

7. The radial opposed migration classifier of claim 1, wherein the discharged particles that travel through the channel are classified based on a property of the discharged particles.

8. The radial opposed migration classifier of claim 7, wherein the property of the discharged particles is a size, mass or charge of the discharged particles.

9. A method for separating particles comprising:
   introducing a sample, comprising one or more particles suspended within a sample fluid, from a flow distributor channel into to a classification channel wherein the flow distributor channel comprises a narrowing gap leading into the classification channel;
   passing the sample through the classification channel, wherein the classification channel comprises a first circular wall and a second circular wall that are both permeable to a flow of fluid;
   introducing a cross-flow fluid to the classification channel through one of the permeable circular walls, wherein the cross-flow fluid flows at a first velocity and exits in a first direction through the other permeable circular wall;
   applying an imposed field on the one or more particles in a second direction counter to the first direction of the cross-flow fluid, wherein the imposed field causes the one or more particles to migrate at a second velocity opposite and/or equal to the first velocity of the cross-flow fluid; and
   discharging the particles that travel through the channel.

10. The method of claim 9, wherein the sample is introduced tangentially into the flow distributor channel.

11. The method of claim 9, wherein the flow distributor channel introduces the sample into the classification channel through a same plane as the first circular wall and further wherein the particles that travel through the channel are discharged through a central outlet on the same plane as the first circular wall.

12. The method of claim 9, wherein the imposed field is an electric field.

13. The method of claim 12, wherein the particles are introduced into the classification channel at an electric potential and discharged from the radial opposed migration classifier at the same electric potential.

14. The method of claim 12, wherein the particles are discharged at an electrical ground voltage.

15. The method of claim 9, further comprising classifying the discharged particles that travel through the channel based on a property of the discharged particles.

16. The method of claim 15, wherein the property of the discharged particles is a size, mass or charge of the discharged particles.

17. The radial opposed migration classifier of claim 1, wherein classified particles pass through a permeable screen when output from the radial opposed migration classifier.

18. The method of claim 9, wherein the discharged particles pass through a permeable screen when output from classification channel.

19. The radial opposed migration classifier of claim 1, wherein:
    a temperature of the sample fluid is changed by changing a temperature of the cross-flow fluid.

20. The method of claim 9, wherein a temperature of the sample fluid is changed by changing a temperature of the cross-flow fluid.

21. The radial opposed migration classifier of claim 1, wherein:
    vapors in the sample fluid are replaced with a vapor-less cross-flow fluid.

22. The method of claim 9, wherein:
    vapors in the sample fluid are replaced with a vapor-less cross-flow fluid.

23. The radial opposed migration classifier of claim 1, wherein:
    one or more of the particles that reach the first circular wall or the second circular wall are removed from the sample fluid by:
       deposition on and adhesion to the first circular wall or the second circular wall; or
       passing through the first circular wall or the second circular wall.

24. The method of claim 9, further comprising:
    removing one or more of the particles that reach the first circular wall or the second circular from the sample fluid by:
       deposition on and adhesion to the first circular wall or the second circular wall; or
       passing through the first circular wall or the second circular wall.

25. A radial opposed migration classifier comprising:
- a classification channel through which passes a sample comprising one or more gas ions suspended in a gas mixture, the classification channel comprising a first circular wall and a second circular wall that are both permeable to a flow of gas;
- a flow distributor channel for introducing the gas mixture into the classification channel;
- a cross-flow gas that enters the classification channel through one of the permeable circular walls, wherein the cross-flow gas flows at a first velocity and exits in a first direction through the other permeable circular wall, and wherein a temperature of the gas mixture is changed by changing a temperature of the cross-flow gas;
- an imposed field that is applied on the one or more gas ions in a second direction counter to the first direction of the cross-flow gas, wherein the imposed field causes the one or more of the gas ions to migrate at a second velocity opposite and/or equal to a first velocity of the cross-flow gas; and
- wherein the gas ions that travel through the channel are discharged from the radial opposed migration classifier.

26. The radial opposed migration classifier of claim 25, further comprising:
- a first flow measuring device that measures a first flow rate of the sample into the radial opposed migration classifier;
- a second flow measuring device that measures a second flow rate of classified gas ions output from the radial opposed migration classifier;
- wherein the first flow rate and the second flow rate are balanced by adjusting a regulator; and
- wherein the classified gas ions output from the radial opposed migration classifier are input into a mass spectrometer to detect and analyze the classified gas ions.

27. The radial opposed migration classifier of claim 25, wherein:
- vapors in the gas mixture are replaced with a vapor-less cross-flow gas.

28. The radial opposed migration classifier of claim 25, wherein:
- one or more of the gas ions that reach the first circular wall or the second circular wall are removed from the gas mixture by:
  - deposition on and adhesion to the first circular wall or the second circular wall; or
  - passing through the first circular wall or the second circular wall.

* * * * *